(12) United States Patent
Griffith et al.

(10) Patent No.: US 9,427,255 B2
(45) Date of Patent: Aug. 30, 2016

(54) APPARATUS FOR INTRODUCING A STEERABLE CAMERA ASSEMBLY INTO A PATIENT

(75) Inventors: David B. Griffith, Cincinnati, OH (US); Sean P. Conlon, Loveland, OH (US); William B. Weisenburgh, II, Maineville, OH (US); Christopher J. Hess, Cincinnati, OH (US); Kempton K. Carroll, II, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 164 days.

(21) Appl. No.: 13/470,781

(22) Filed: May 14, 2012

(65) Prior Publication Data
US 2013/0303851 A1    Nov. 14, 2013

(51) Int. Cl.
*A61B 1/04* (2006.01)
*A61B 17/34* (2006.01)
*A61B 1/00* (2006.01)
*A61B 17/00* (2006.01)

(52) U.S. Cl.
CPC ....... *A61B 17/3421* (2013.01); *A61B 17/3462* (2013.01); *A61B 1/00158* (2013.01); *A61B 1/041* (2013.01); *A61B 2017/00283* (2013.01); *A61B 2017/3445* (2013.01)

(58) Field of Classification Search
CPC .............. A61B 2017/0237; A61B 2017/3445
USPC ........................ 600/114, 118, 153–159, 138; 604/167.01–167.06
See application file for complete search history.

(56) References Cited

U.S. PATENT DOCUMENTS

| | | | |
|---|---|---|---|
| 645,576 A | 3/1900 | Telsa |
| 649,621 A | 5/1900 | Tesla |
| 787,412 A | 4/1905 | Tesla |
| 1,039,354 A | 9/1912 | Bonadio |

(Continued)

FOREIGN PATENT DOCUMENTS

| AU | 666310 B2 | 2/1996 |
|---|---|---|
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Anhtuan T Nguyen
*Assistant Examiner* — Timothy J Neal

(57) ABSTRACT

A cannula assembly including a seal for an endoscopic internal magnetic camera tether. The seal may include stacked compliant membranes with an aperture in each membrane through which a camera tether may pass. The apertures may overlap. The at least one aperture may be arranged as a slit. Each of the apertures may comprise a wedge-shaped gap. The membranes may include engagement members that couple to engagement members on the cannula assembly. The cannula assembly may provide separate ports for the camera tethers and for a trocar or other endoscopic instrument passing through the cannula assembly. The cannula assembly also may include a rotating housing with two openings and a seal arranged in each opening. The cannula assembly may include a sleeve that encases a cannula tube. The sleeve may include a seal on its end and a channel on its periphery through which a camera tether may pass.

22 Claims, 33 Drawing Sheets

(56) References Cited

U.S. PATENT DOCUMENTS

| | | |
|---|---|---|
| 1,127,948 A | 2/1915 | Wappler |
| 1,482,653 A | 2/1924 | Lilly |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,790,624 A | 12/1988 | Van Hoye et al. |
| 4,815,450 A | 3/1989 | Patel |
| 4,823,794 A | 4/1989 | Pierce |
| 4,829,999 A | 5/1989 | Auth |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |

(56) References Cited

U.S. PATENT DOCUMENTS

| | | |
|---|---|---|
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,376,077 A * | 12/1994 | Gomringer .............. 604/167.06 |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,478,352 A | 12/1995 | Fowler |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,533,418 A | 7/1996 | Wu et al. |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,591,205 A | 1/1997 | Fowler |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,601,602 A | 2/1997 | Fowler |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |

(56) References Cited

U.S. PATENT DOCUMENTS

| | | |
|---|---|---|
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,800,451 A | 9/1998 | Buess et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |

(56) References Cited

U.S. PATENT DOCUMENTS

| | | |
|---|---|---|
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,640 A | 3/2000 | Corace et al. |
| 6,036,685 A | 3/2000 | Mueller |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,120 B1 * | 5/2003 | Green et al. ............ 604/167.04 |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |

(56) References Cited

U.S. PATENT DOCUMENTS

| | | |
|---|---|---|
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |

(56) References Cited

U.S. PATENT DOCUMENTS

| | | |
|---|---|---|
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |

(56) References Cited

U.S. PATENT DOCUMENTS

| | | |
|---|---|---|
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |
| 7,749,161 B2 | 7/2010 | Beckman et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,447 B2 | 9/2010 | Dann et al. |
| 7,794,475 B2 | 9/2010 | Hess et al. |
| 7,798,386 B2 | 9/2010 | Schall et al. |
| 7,815,565 B2 | 10/2010 | Stefanchik et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,833,156 B2 | 11/2010 | Williams et al. |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,021,362 B2 | 9/2011 | Deem et al. |
| 8,029,504 B2 | 10/2011 | Long |
| 8,034,046 B2 | 10/2011 | Eidenschink |
| 8,037,591 B2 | 10/2011 | Spivey et al. |
| 8,048,067 B2 | 11/2011 | Davalos et al. |
| 8,052,699 B1 | 11/2011 | Sherwinter |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,070,759 B2 | 12/2011 | Stefanchik et al. |
| 8,070,804 B2 | 12/2011 | Hyde et al. |
| 8,075,572 B2 | 12/2011 | Stefanchik et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,100,922 B2 | 1/2012 | Griffith |
| 8,114,072 B2 | 2/2012 | Long et al. |
| 8,114,119 B2 | 2/2012 | Spivey et al. |
| 8,118,821 B2 | 2/2012 | Mouw |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,206,295 B2 | 6/2012 | Kaul |
| 8,211,125 B2 | 7/2012 | Spivey |
| 8,221,310 B2 | 7/2012 | Saadat et al. |
| 8,241,204 B2 | 8/2012 | Spivey |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |
| 8,303,581 B2 | 11/2012 | Arts et al. |
| 8,308,738 B2 | 11/2012 | Nobis et al. |
| 8,317,806 B2 | 11/2012 | Coe et al. |
| 8,328,836 B2 | 12/2012 | Conlon et al. |
| 8,337,394 B2 | 12/2012 | Vakharia |
| 8,337,492 B2 | 12/2012 | Kunis et al. |
| 8,353,487 B2 | 1/2013 | Trusty et al. |
| 8,357,170 B2 | 1/2013 | Stefanchik |
| 8,361,066 B2 | 1/2013 | Long et al. |
| 8,361,112 B2 | 1/2013 | Carroll, II et al. |
| 8,403,926 B2 | 3/2013 | Nobis et al. |
| 8,409,200 B2 | 4/2013 | Holcomb et al. |
| 8,425,505 B2 | 4/2013 | Long |
| 8,430,811 B2 | 4/2013 | Hess et al. |
| 8,449,538 B2 | 5/2013 | Long |
| 8,480,657 B2 | 7/2013 | Bakos |
| 8,480,689 B2 | 7/2013 | Spivey et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,523,939 B1 | 9/2013 | Hausen |
| 8,529,563 B2 | 9/2013 | Long et al. |
| 8,545,396 B2 | 10/2013 | Cover et al. |
| 8,568,410 B2 | 10/2013 | Vakharia et al. |
| 8,579,897 B2 | 11/2013 | Vakharia et al. |
| 8,608,652 B2 | 12/2013 | Voegele et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |

(56) References Cited

U.S. PATENT DOCUMENTS

| | | |
|---|---|---|
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0018373 A1 | 1/2003 | Eckhardt et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0070947 A1* | 3/2005 | Franer et al. ............... 606/185 |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0240249 A1 | 10/2005 | Tu et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |

(56) References Cited

U.S. PATENT DOCUMENTS

| | | |
|---|---|---|
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |

(56) References Cited

U.S. PATENT DOCUMENTS

| | | |
|---|---|---|
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0208280 A1 | 8/2008 | Lindenthaler et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0299135 A1 | 12/2009 | Spivey |
| 2009/0299143 A1 | 12/2009 | Conlon et al. |
| 2009/0299406 A1 | 12/2009 | Swain et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049223 A1 | 2/2010 | Granja Filho |
| 2010/0056862 A1 | 3/2010 | Bakos |

(56) References Cited

U.S. PATENT DOCUMENTS

| | | |
|---|---|---|
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1* | 4/2010 | Fowler et al. ............... 600/114 |
| 2010/0087705 A1* | 4/2010 | Byers et al. ................. 600/104 |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152746 A1 | 6/2010 | Ceniccola et al. |
| 2010/0179510 A1 | 7/2010 | Fox et al. |
| 2010/0191050 A1 | 7/2010 | Zwolinski |
| 2010/0191267 A1 | 7/2010 | Fox |
| 2010/0198149 A1 | 8/2010 | Fox |
| 2010/0198248 A1 | 8/2010 | Vakharia |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152610 A1 | 6/2011 | Trusty et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0289857 A1 | 11/2012 | Toth et al. |
| 2012/0330306 A1 | 12/2012 | Long et al. |
| 2013/0030430 A1 | 1/2013 | Stewart et al. |
| 2013/0090666 A1 | 4/2013 | Hess et al. |
| 2013/0158348 A1 | 6/2013 | Nobis et al. |
| 2013/0217970 A1 | 8/2013 | Weisenburgh, II et al. |
| 2013/0245356 A1 | 9/2013 | Fernandez et al. |
| 2013/0261389 A1 | 10/2013 | Long |
| 2014/0012247 A1 | 1/2014 | Bakos et al. |
| 2014/0031813 A1 | 1/2014 | Tellio et al. |
| 2014/0039491 A1 | 2/2014 | Bakos et al. |
| 2014/0039492 A1 | 2/2014 | Long |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 B1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 86/07543 A1 | 12/1986 |

(56) References Cited

FOREIGN PATENT DOCUMENTS

| | | |
|---|---|---|
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/080062 A2 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |
| WO | WO 2012/031204 A2 | 3/2012 |

OTHER PUBLICATIONS

Ethicon, Inc., "Wound Closure Manual: Chapter 3 (The Surgical Needle)," 15 pages, (1994).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

(56) References Cited

OTHER PUBLICATIONS

H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis col. Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavč ič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at Sages Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.
U.S. Appl. No. 13/586,439, filed Aug. 15, 2012.
U.S. Appl. No. 13/586,422, filed Aug. 15, 2012.
U.S. Appl. No. 13/778,582, filed Feb. 27, 2013.
U.S. Appl. No. 14/061,431, filed Oct. 23, 2013.

\* cited by examiner

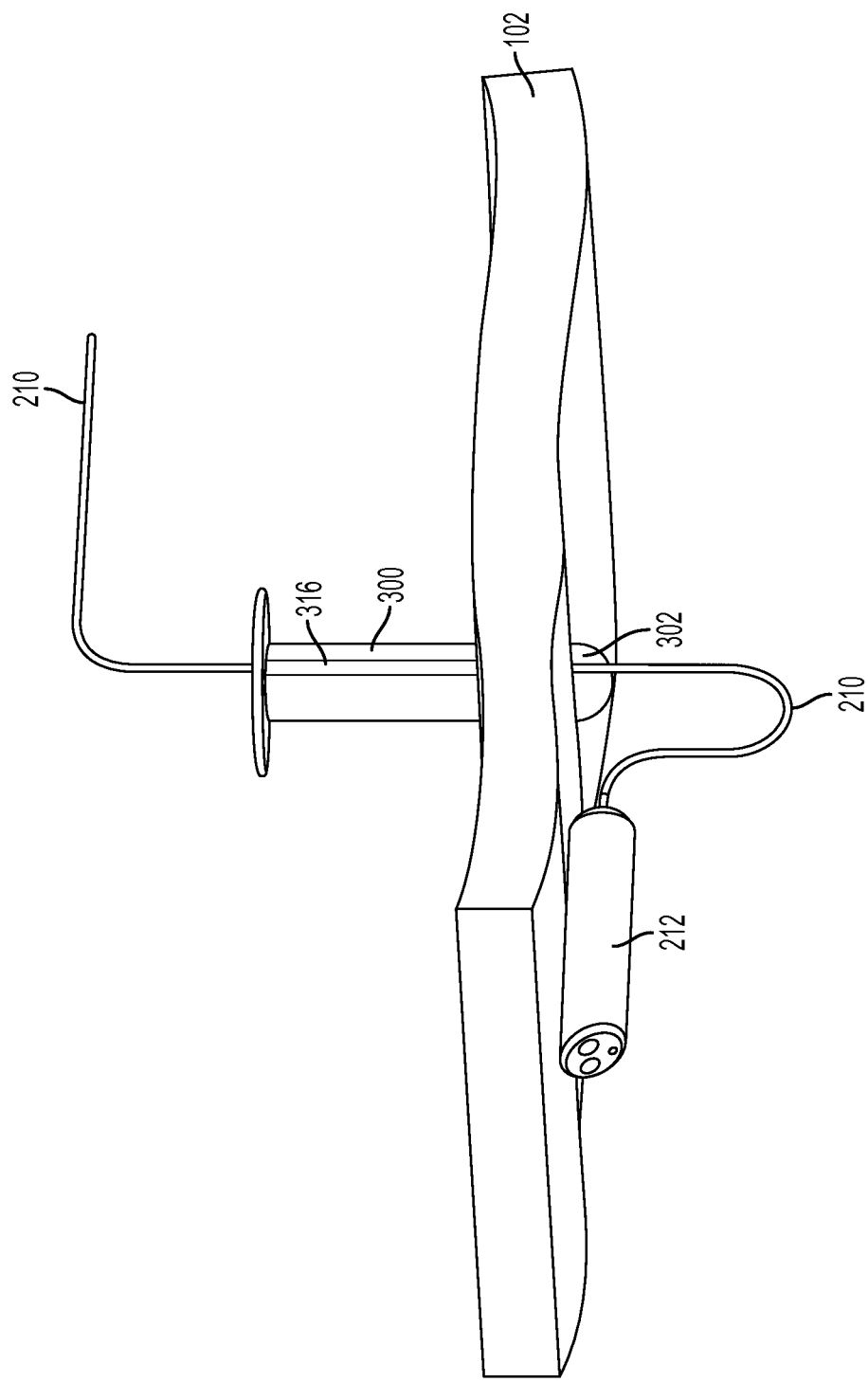

APPARATUS FOR INTRODUCING A STEERABLE CAMERA ASSEMBLY INTO A PATIENT

BACKGROUND

Endoscopic surgery in the abdominal cavity of an animal, such as, for example, a human, may include insufflating the abdomen to create a space in which surgeons may introduce endoscopic surgical instruments. Access to the abdomen may be created with a trocar assembly, which may include a hollow cannula and a solid shaft passing through the cannula. The solid shaft may include a sharp tip that pierces the abdominal wall to form an otomy and that guides the cannula partially into the insufflated abdominal cavity. After the cannula is in place in the otomy, the solid shaft may be withdrawn from the cannula, leaving a passage through the cannula that the surgeon may use to access the abdominal cavity using endoscopic surgical devices. The cannula may include a seal, such as a duck bill seal, at its distal end that is biased in a closed position to prevent or retard the escape of gases insufflating the abdomen. A surgeon chooses a trocar size that closely fits the endoscopic tools he intends to introduce therethrough. For example, if the endoscopic tool to be used has a diameter of 14 millimeters, then a cannula having an inner diameter of slightly more than 14 millimeters would be used. The endoscopic tool passes through the cannula and opens the seal on the cannula. The close sizing between the endoscopic tool and the cannula prevents or retards the escape of the gasses insufflating the abdomen that would otherwise pass through the open seal.

Magnetic anchoring and guidance systems (MAGS) have been developed for use in minimally invasive procedures. MAGS include an internal device attached in some manner to a surgical instrument, laparoscope or other camera or viewing device, and an external hand held device or external control unit ("ECU") for controlling the movement of the internal device. Each of the external and internal devices has magnets which are magnetically coupled to each other across, for example, a patient's abdominal wall. In the current systems, the external magnet may be adjusted by varying the height of the external magnet.

The camera is attached to one or more tethers that provide power to the camera's electronics, image date, and, optionally, water or gases. The tethers lead out through the cannula and pass through the seal on the cannula. The presence of the tether prevents the seal on currently-available cannulas from closing, thereby creating a leak that enables the insufflation gases to escape when other endoscopic surgical instruments are not placed in the cannula.

The foregoing discussion is intended only to illustrate various aspects of the related art in the field of the invention at the time, and should not be taken as a disavowal of claim scope.

SUMMARY OF THE INVENTION

Embodiments described herein provide a cannula assembly with a seal for a tether of an internal magnetic camera. The cannula assembly may include a housing that includes a distal opening and a proximal opening with a passage therebetween. The housing may be configured to have a cannula tube attached in a manner that the cannula tube is in fluid communication with the distal opening. A plurality of compliant membranes may be arranged as a stack anywhere in the passage or in the proximal or distal openings. The compliant membranes may be made of any compliant material, such as, for example, silicone, latex, or rubber. In various embodiments, the stack may include two compliant membranes. In various other embodiments, the stack may include three compliant membranes. Each membrane includes an aperture that may open to accommodate an internal magnetic camera or its tether, or any other endoscopic device that is passed through the membranes. The apertures may be arranged such that, when the compliant membranes are stacked, each aperture does not overlap with remaining apertures.

In certain embodiments in which the stack includes at least three compliant membranes, one of the apertures may comprise a slit, and the compliant membrane in which the slit is formed is sandwiched between two membranes having apertures of a different configuration, such as, for example, apertures having circular shapes. In certain other embodiments in which the stack includes at least three compliant membranes, each aperture may comprise a wedge-shaped gap formed in its respective compliant membrane, and, the compliant membranes may be arranged such that, when they are arranged in a stack, each wedge-shaped gap does not overlap with remaining wedge-shaped gaps.

In various embodiments, the membranes may include a plurality of engagement members that are configured to couple to engagement members in the passage or one of the proximal and distal openings of the cannula housing. In certain embodiments, coupling of the respective membranes may result in each of the compliant membranes being stretched in a region between its engagement members. In certain embodiments, the engagement members of the cannula housing may comprise a plurality of posts around a periphery of the passage or one of the proximal or distal openings, and the engagement members on each of the compliant membranes may comprise a plurality of holes around the periphery each membrane that fit over the posts. A retaining ring may be placed on the membranes to retain them in the passage or in the proximal or distal openings.

In various embodiments, the cannula housing may be configured include an upper housing in fluid communication with the proximal opening. The upper housing may include a port or several ports configured to receive tethers of the camera, and the ports are distinct from an opening in the upper housing that is configured to receive other endoscopic instruments. The ports may include gaskets that provide a tight seal against the tethers.

In various embodiments, the cannula housing may include a first face and a second face, and each of the first and second faces includes a proximate opening. Each of the two proximate openings has a plurality of compliant membranes and apertures. The two proximate openings are at an angle relative to each other, and each of the two openings is in fluid communication with the passage in the cannula housing. The housing is configured to rotate in a bracket between a first position and a second position. In the first position, a first of the two proximate openings is aligned with the distal opening via the passage. In the second position, a second of the proximate openings is aligned with the distal opening via the passage.

In various embodiments, a cannula assembly includes a cannula tube and the seal comprises a sleeve encasing at least a portion of the tube. The sleeve may include a seal at its distal end, such as, for example, a duck bill seal or a clam shell seal. The sleeve also may include a channel on its periphery and substantially parallel to a longitudinal axis of the cannula tube. The channel is configured to receive a tether for an internal magnetic camera. The channel may include open distal and proximal ends such that the tether bypasses the seal. In use, after the surgeon inserts the cannula tube into a body cavity through an otomy, the cannula tube may be removed, leaving the sleeve positioned in the otomy. The seal at the distal end of the sleeve inhibits the escape of insufflation gases from the body cavity. The surgeon may then push the camera into the body cavity through the sleeve. After the camera is positioned in the body cavity, the camera tether may be pushed into the tether such that it is out of the way for additional endoscopic instruments that may be placed in the sleeve.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 10G is a perspective view of the cannula sleeve of FIG. 10D with a camera and tether;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION OF THE INVENTION

Figure 1A:
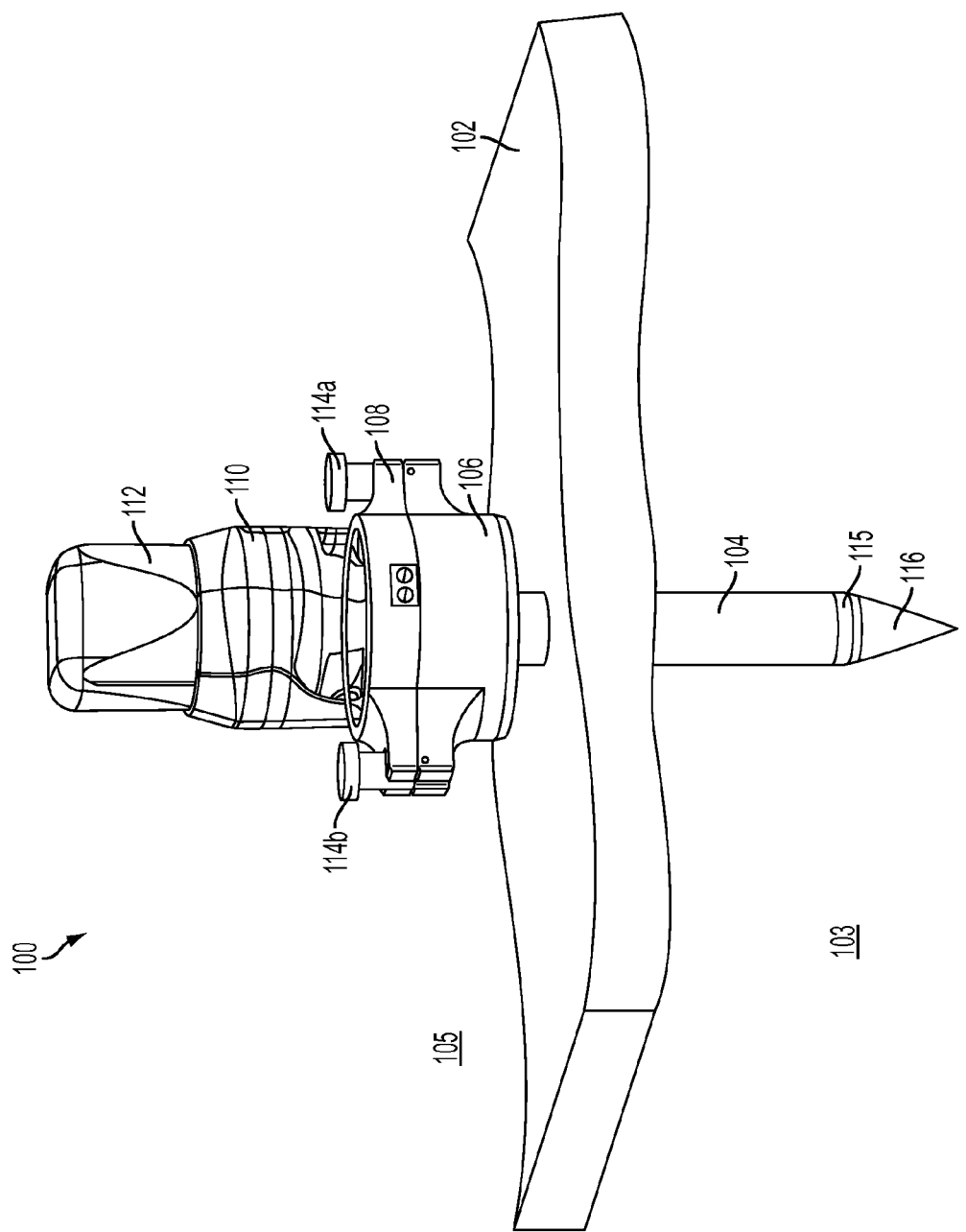
FIG. 1A is a perspective view of a trocar and obturator assembly according to an embodiment of the present invention.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

In describing and claiming the present invention, the following terminology will be used in accordance with the definitions set out below.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located farthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

As used herein, the term "biocompatible" includes any material that is compatible with the living tissues and system(s) of a patient by not being substantially toxic or injurious and not known to cause immunological rejection. "Biocompatibility" includes the tendency of a material to be biocompatible.

As used herein, the term "patient" refers to any human or animal on which a suturing procedure may be performed. As used herein, the term "internal site" of a patient means a lumen, body cavity or other location in a patient's body including, without limitation, sites accessible through natural orifices or through incisions.

Figure 1B:
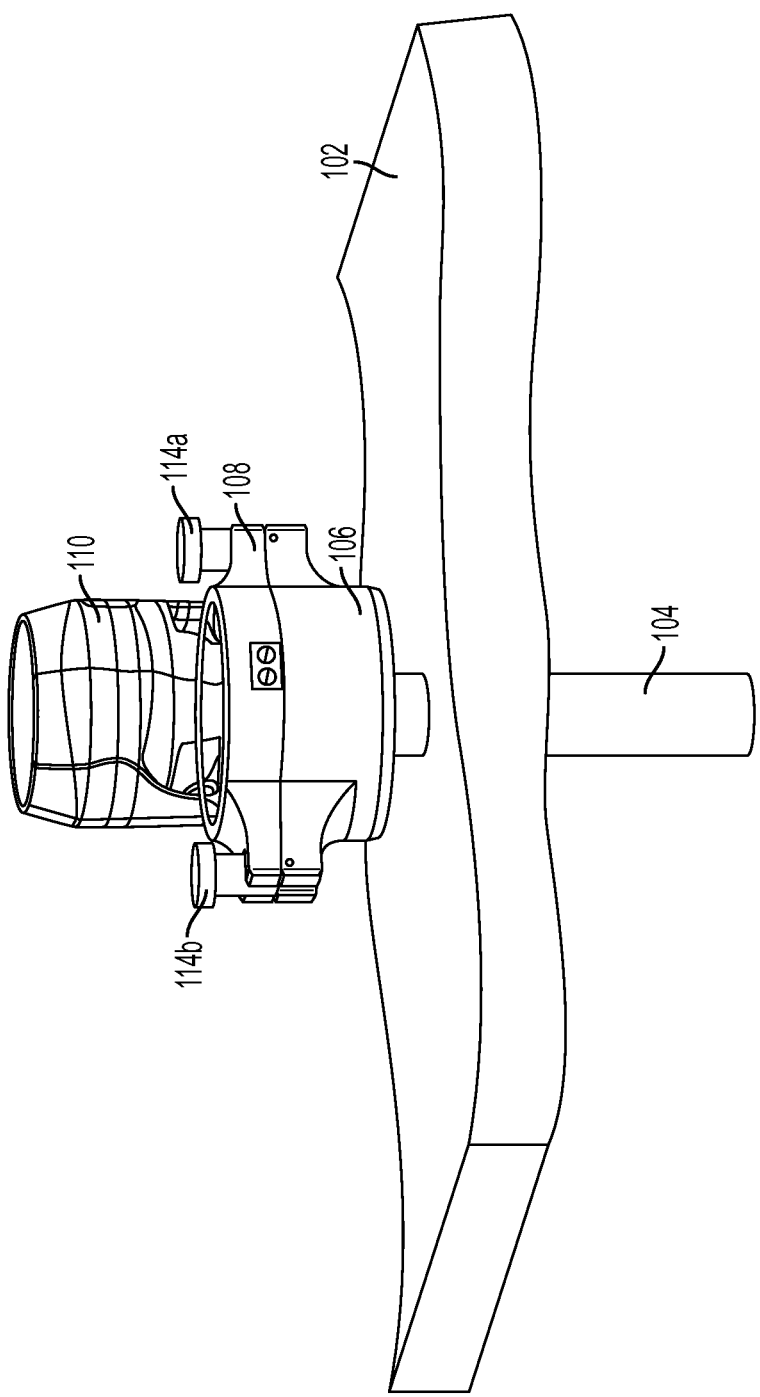
FIG. 1B is a perspective view of the trocar assembly of FIG. 1A with an obturator assembly removed.

FIG. 1A is a perspective view of a surgical trocar assembly 100, such as the trocar assembly described in U.S. Pat. No. 5,817,061, the relevant portions of which are incorporated by reference, modified to incorporate an embodiment of the present invention, passing through tissue 102 of an animal, such as, for example, a human. The surgical trocar assembly 100 includes a cannula tube 104 attached to a lower cannula housing 106. An upper cannula housing 108 is mounted on top of the lower cannula housing 106 and is held in place by thumb screws 114a and 114b. A cannula head 110 is attached to the top of the upper cannula housing 108. The cannula head 110 may be permanently attached to the upper cannula housing 108, for example, by glue, epoxy, or other bonding agents, or by welding, such as ultrasonic welding. Alternatively, the cannula head 110 may be removably attached to the upper cannula housing 108, for example, by screws, bolts, clips, or the like. The cannula tube 104 is hollow, and the lower cannula housing 106, upper cannula housing 108, and cannula head 110 each include an aperture aligned with the hollow cannula tube 104 such that an obturator shaft 115 may pass therethrough. The obturator shaft 115 may terminate at a distal end with an obturator tip 116. The obturator shaft 115 is attached at its proximal end to an obturator grip 112. The obturator grip 112 may be attachable to the cannula head 110, for example, by a spring-loaded clip (not shown), such that the trocar assembly 100 may be manipulated as a whole. In FIG. 1A, a substantial portion of the cannula tube 104, and the obturator shaft 115, and the obturator tip 116 have penetrated the tissue 102 and have passed into an interior body cavity 103, such as, for example, an abdominal cavity. The lower cannula housing 106, upper cannula housing 108, cannula head 110, and obturator grip 112 remain in an exterior space 105. When the trocar assembly 100 is positioned as shown in FIG. 1A, the obturator shaft 115 may be removed from the cannula tube 104. FIG. 1B is a perspective view of the surgical trocar subassembly 100 with the obturator shaft 115 and obturator grip 112 so removed.

Figure 2A:
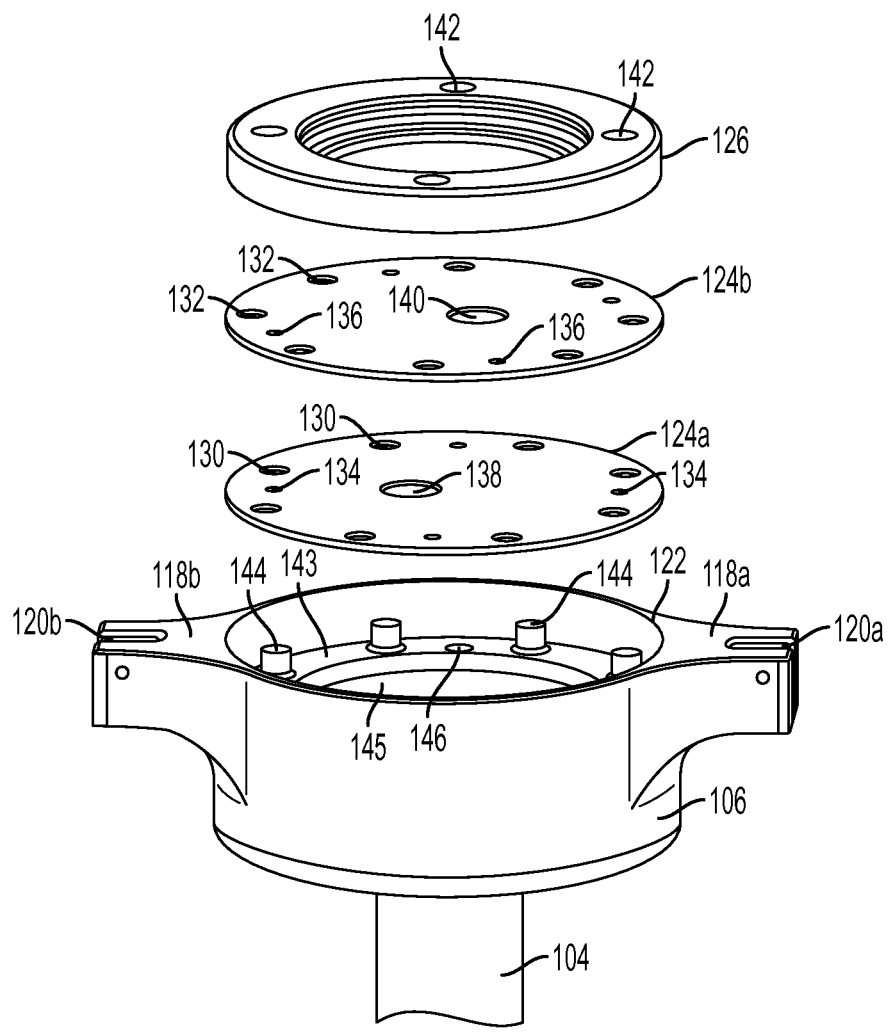
FIG. 2A is a perspective exploded view of a cannula housing and compliant membranes according to an embodiment of the present invention.

FIG. 2A is a perspective exploded view of the lower cannula housing 106 and sealing membranes 124a and 124b disposed therein. The lower cannula housing 106 may be hollow, including a proximal opening 122 that communicates with the upper cannula housing 108 (not shown in FIG. 2A) and a passage 145 that communicates with the hollow cannula tube 104. An engagement surface 143 in the passage 145 includes several engagement members, such as pins, clips, or anchors 144. For example, the engagement members 144 may be posts, such as, for example, cylindrical posts around the periphery of the engagement surface 143. A plurality of membranes 124a and 124b (in the embodiment shown in FIG. 2A, two membranes) may be placed in the passage and secured to the engagement surface 143. The membranes at least partially block fluid communication between the proximal opening 122 and the passage 145. Each membrane preferably may be made of a compliant material, such as, for example, silicone, latex, or rubber. Membrane 124a may include engagement members 130 on its periphery that compliment the engagement members 144 on the engagement surface. Membrane 124b may include engagement members 132 on its periphery that compliment the engagement members 144 on the engagement surface. For example, each of the engagement members 130, 132 may comprise a series of holes arranged on the periphery of respective membranes 124a and 124b. The engagement members 130, 132 on respective membranes 124a and 124b align with the engagement members 144 on the engagement surface 143, and placement of the engagement members 130, 132 over the anchors result in each membrane 124a and 124b being aligned in a fixed facing relationship relative to remaining membranes. Placement of the engagement members 130, 132 over the engagement members 144 also may result in the membranes 124a and 124b being stretched. A retaining ring 126 may be placed on top of the membranes 124a and 124b to hold the membranes 124a and 124b in place. The retaining ring 126 may include holes 142 sized to accommodate screws or other fasteners (not shown). The fasteners also may pass through holes 136 in membrane 124b and holes 134 in membrane 124a to anchor in holes 146 in the engagement surface 143. Membrane 124a includes an aperture 138 and membrane 124b includes an aperture 140. When the membranes 124a and 124b are installed in the lower cannula housing 106, the apertures 138 and 140 preferably are not aligned, i.e., the apertures 138 and 140 do not overlap. For example, the apertures 138, 140 may be disposed proximate to centers of the membranes 124a and 124b, but each membrane's aperture is offset from the membrane's center such that the aperture 138 of the first membrane 124a does not overlap with the aperture 140 of the second membrane 124b.

Figure 2B:
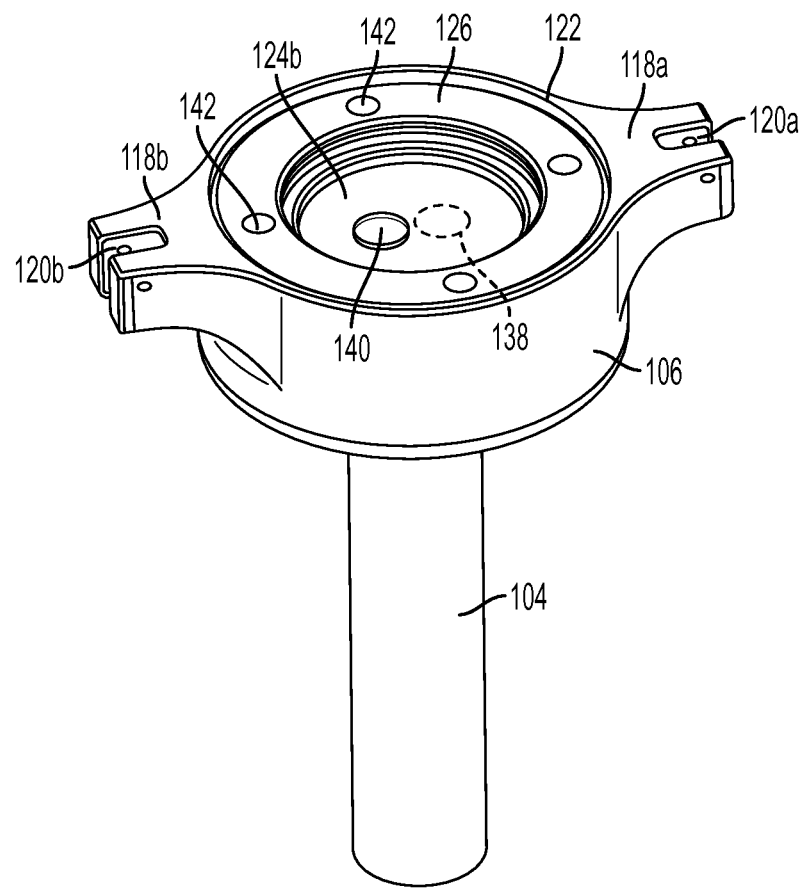
FIG. 2B is a perspective view of the cannula housing and compliant membranes of FIG. 2A.
Figure 2C:
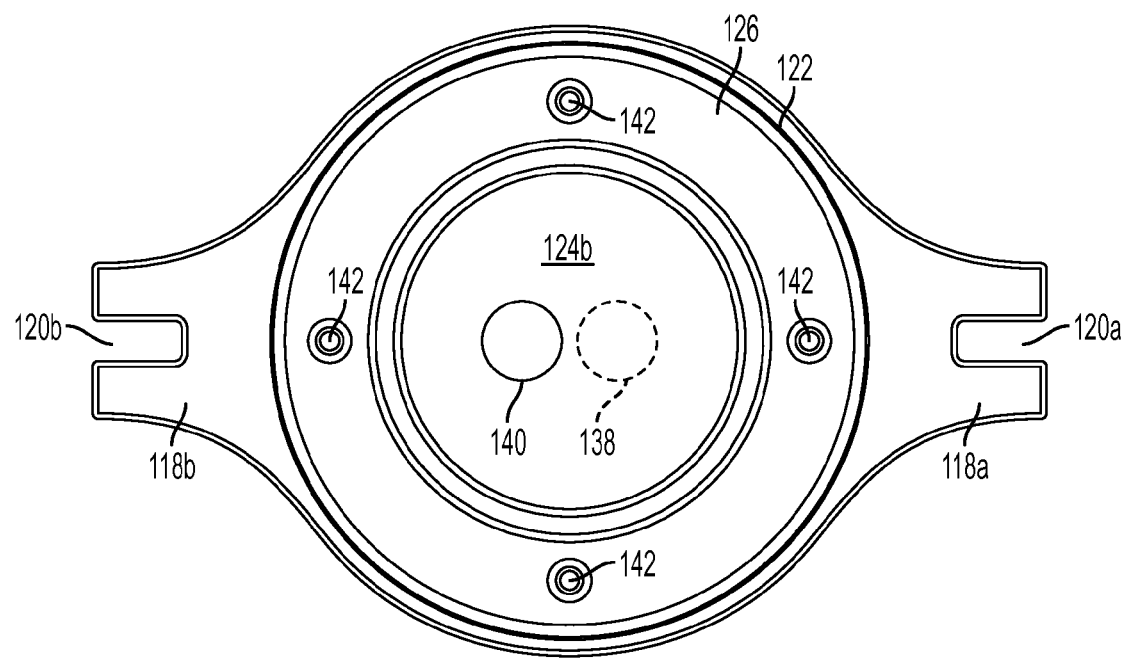
FIG. 2C is a top view of the cannula housing and compliant membranes of FIG. 2B.

FIGS. 2B and 2C are perspective and top views, respectively, of the lower cannula housing of FIG. 2A showing the membranes 124a and 124b and the retaining ring 126 installed. In the installed configuration, the membranes 124a and 124b block the passage 145, and the apertures 138 and 140 in membranes 124a and 124b do not overlap. The lack of an overlap between apertures 138 and 140 provides a torturous path for gases or fluids between the passage 145 and the proximal opening 122 in the lower cannula housing 106. To escape from the cannula tube 104 to the proximal opening 122 in the lower cannula housing 106, gas (generally, an insufflation gas, such as carbon dioxide) must pass through the aperture 138 in the first membrane 124a (which is pressed against the second membrane 124b), travel through the space between the two sandwiched membranes 124a and 124b, and then pass through the aperture 140 in the second membrane. Because the membranes 124a and 124b are stacked on top of each other and because each membrane 124a and 124b is stretched across the anchors 144, the membranes are in close contact with each other. Also, the differential pressure of the insufflation gases in the cannula tube 104 over atmospheric pressure at the proximal opening 122 in the lower cannula housing 106 presses membrane 124a into membrane 124b, thereby maintaining membrane 124a in contact with membrane 124b. This tight path between the membranes 124a and 124b through which the insufflation gases must pass to get from aperture 138 to aperture 140 is a torturous path that inhibits leakage of the insufflation gases.

The membranes 124a and 124b preferably may be made of compliant materials, described above, which enable endoscopic tools to be pushed through the apertures 138, 140 without requiring alignment of a distal end of a tool with the apertures 138, 140. For example, if the obturator shaft 115 and obturator tip 116 are reinserted into the cannula tube, they must pass through the membranes 124a and 124b. The obturator tip 116 pressing on the membranes 124a and 124b will cause the membranes 124a and 124b to stretch, and the stretching will cause the apertures 138, 140 to shift towards the obturator tip 116. Thus, by pushing the obturator tip 116 into the membranes 124a and 124b, the apertures 138, 140 in the membranes 124a and 124b automatically align with the obturator tip 116, thereby enabling the obturator tip 116 and the obturator shaft 115 to pass therethrough.

Figure 3A:
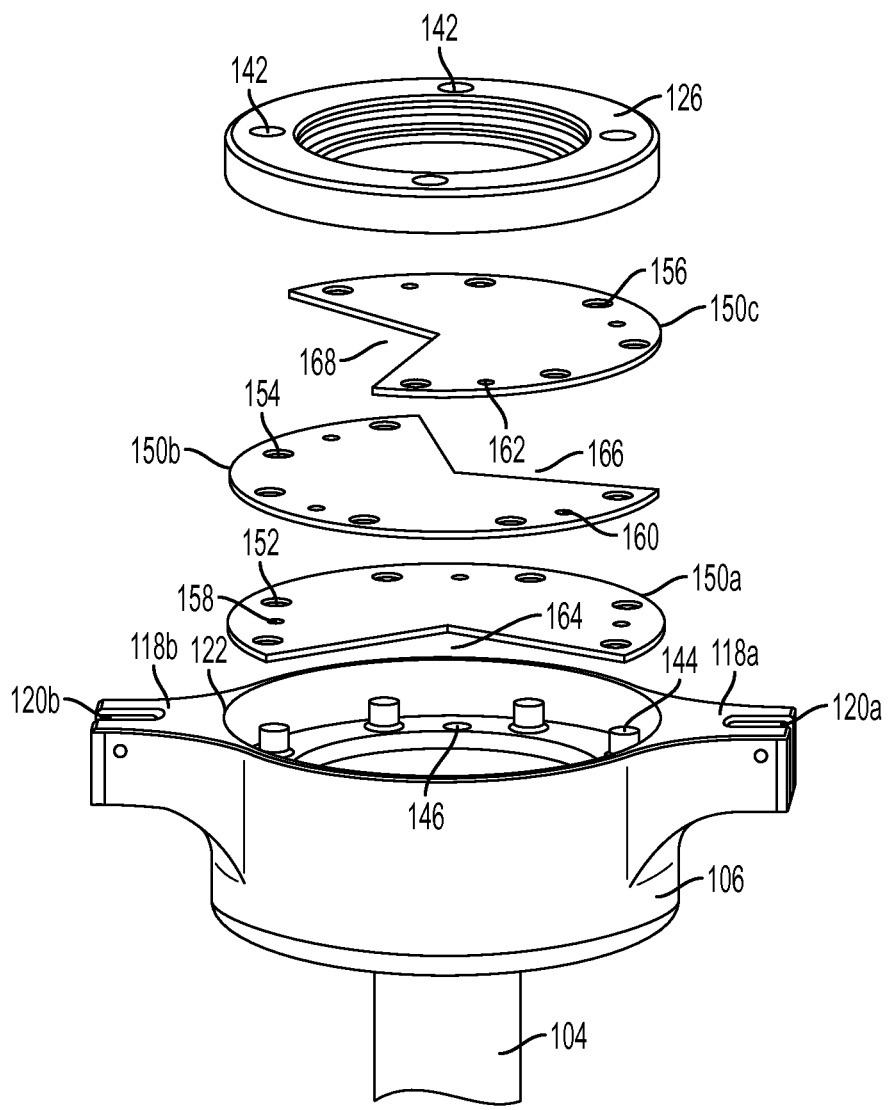
FIG. 3A is a perspective exploded view of a cannula housing and compliant membranes according to another embodiment of the present invention.
Figure 3B:
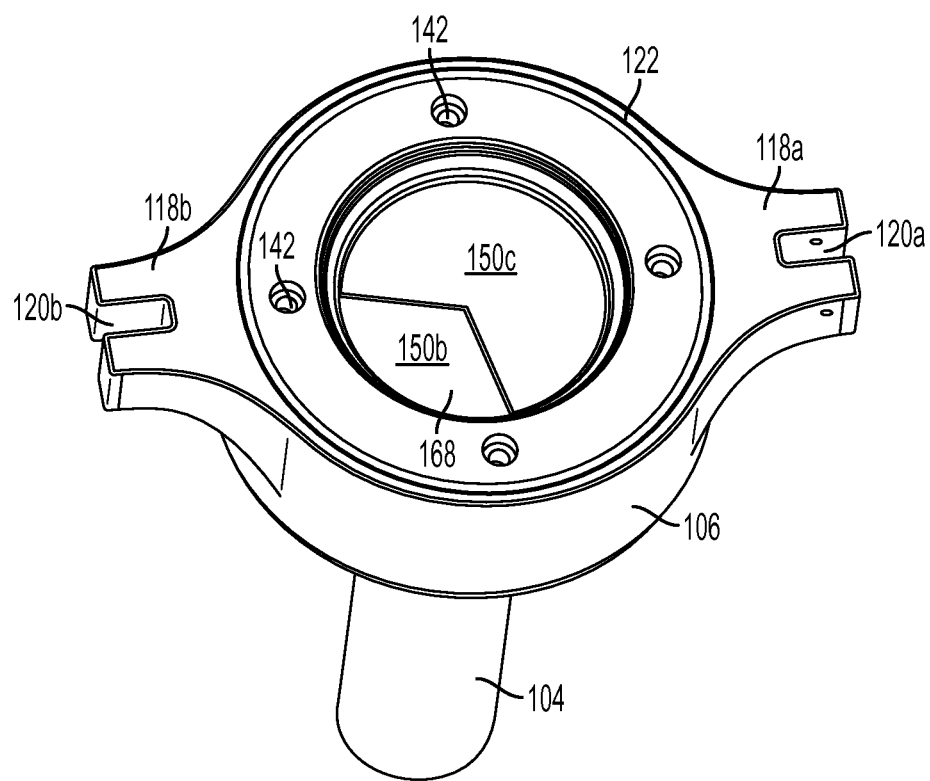
FIG. 3B is a perspective view of the top of the assembled cannula housing and compliant membranes of FIG. 3A.

FIG. 3A is a perspective exploded view of a second embodiment in which there are more than two, for example, three membranes 150a-c. In certain embodiments, such as that shown in FIG. 3A, the membranes have wedge-shaped apertures 164, 166, and 168, respectively. FIG. 3B is a perspective view of the embodiment in FIG. 3A in an installed configuration. Each wedge-shaped aperture 164, 166, 168 does not overlap apertures of adjacent layers and may not overlap the apertures 164, 166, 168 of any other membrane layer. Thus, insufflation gases from the cannula tube 104 must pass between the first membrane 150a and the second membrane 150b, and then between the second membrane 150b and the third membrane 150 to escape to the proximal opening 122 in the lower cannula housing 106 through the apertures 164, 166, and 168. Furthermore, the wedge-shaped apertures 164, 166, 168 preferably do not extend over the center point of the respective membranes 150a-c so that the wedge-shaped apertures 164, 166, 168 do not overlap in any way to form a direct path through which insufflation gases may escape.

Figure 4A:
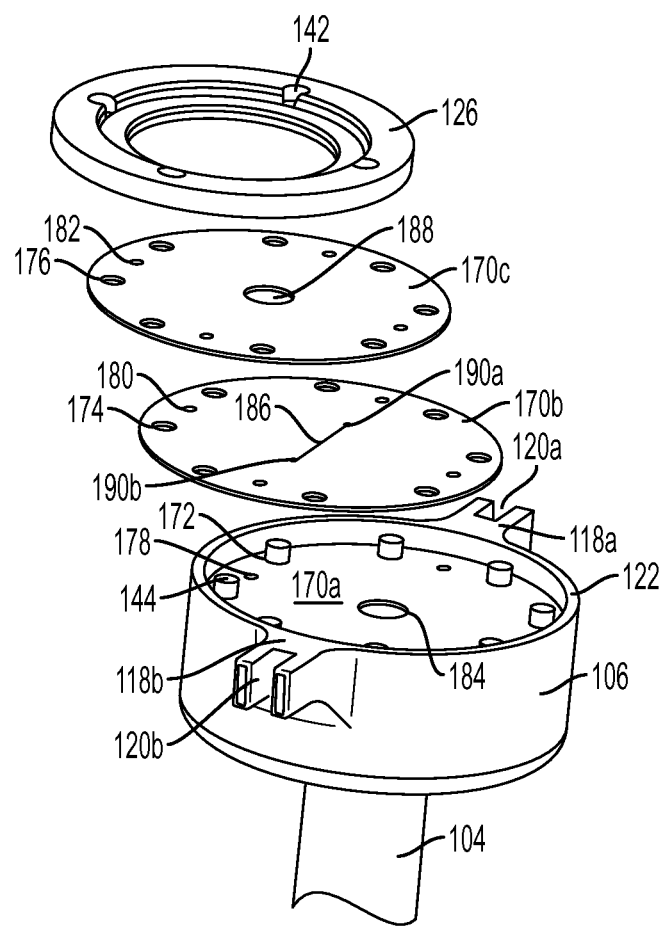
FIG. 4A is a perspective exploded view of a cannula housing and compliant membranes according to another embodiment of the present invention.

FIG. 4A is a perspective partially-exploded view of another embodiment in which there are three membranes 170a (shown installed), 170b, and 170c. Membrane 170a has a circular aperture 184 proximate to its center and membrane 170c also has a circular aperture 188 proximate to its middle. Membrane 170b has a slit 186 as an aperture. For clarity, the slit 186 is shown with a gap between its sides. However, the slit may be formed by cutting a line in the membrane 170b, removing no membrane material or a negligible amount of membrane material such that the slit 186 has no gap when the membrane 170b is not deformed. Additionally, the slit 186 may include relief cuts 190a and 190b at its ends. The relief cuts 190a,b provide for stress relief at ends of the slit 186 when the slit is stretched and enables the slit 186 to stretch to a larger shape without tearing the membrane. FIG. 4D shows a slit 186 without relief cuts 190a and 190b stretched open, e.g., by an endoscopic tool. The size of the opening of slit 186 is limited by the ends. FIG. 4E shows the slit 186 with relief cuts 190a and 190b at end. The relief cuts 190a and 190b enable the slit 186 to open to a larger size.

Figure 4B:
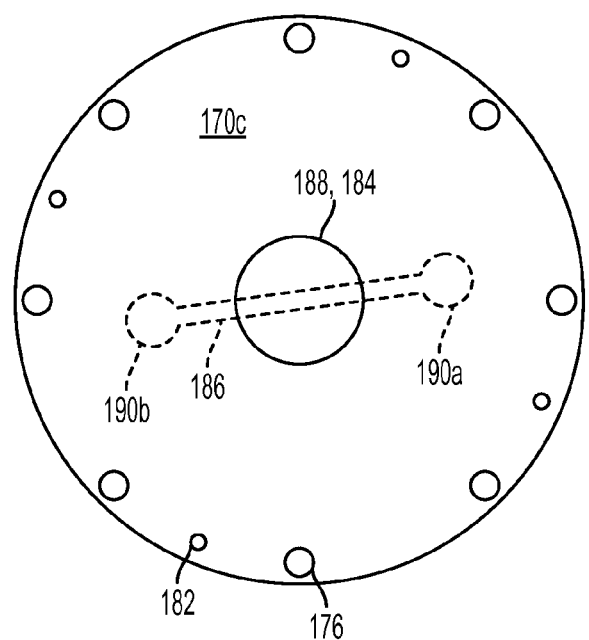
FIG. 4B is a top view of compliant membranes according to another embodiment of the present invention, showing apertures in respective membranes in broken line.
Figure 4C:
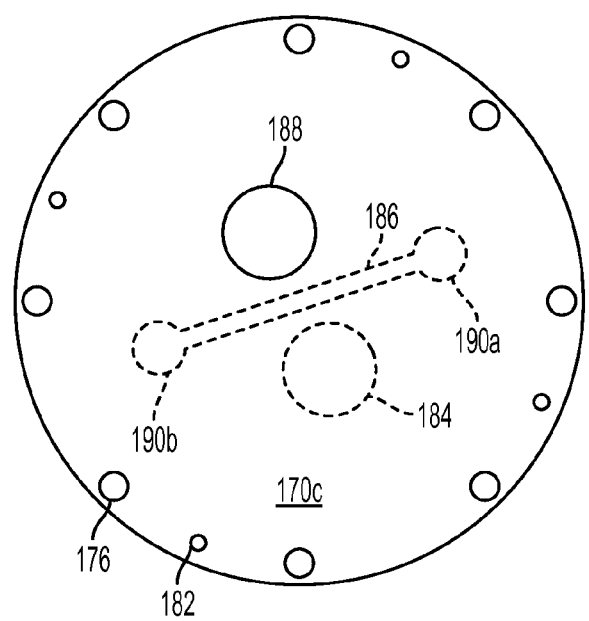
FIG. 4C is a top view of compliant membranes according to another embodiment of the present invention, showing apertures in respective membranes in broken line.
Figure 4D:
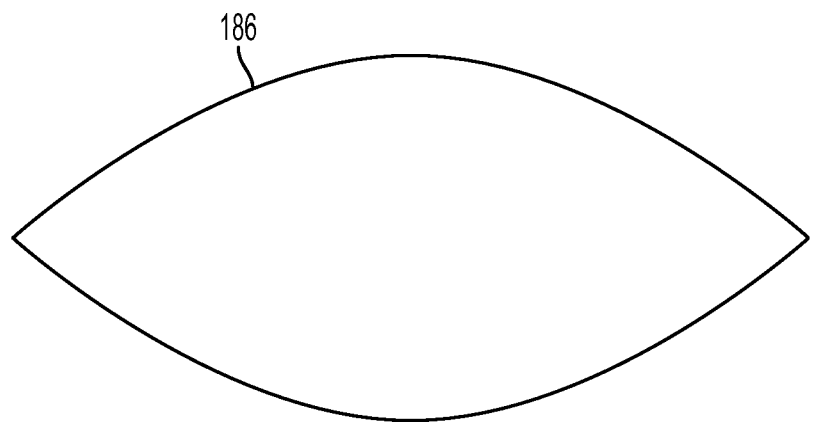
FIG. 4D is a top view of a slit aperture in a compliant membrane with no relief cuts at its ends in a stretched open configuration.
Figure 4E:
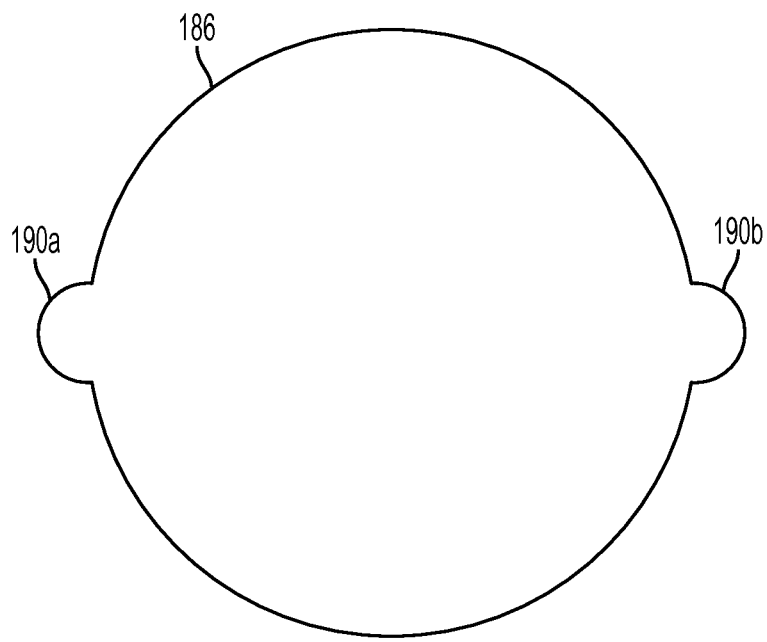
FIG. 4E is a top view of a slit aperture in a compliant membrane with relief cuts at its ends in a stretched open configuration.

In certain embodiments, such as that shown in FIG. 4B, the apertures 184, 186, and 188 may be arranged on their respective membranes 170a, 170b, and 170c such that the apertures 184, 186, and 188 overlap when the membranes 170a, 170b, and 170c are stacked in the lower cannula housing 106. In certain embodiments, such as that shown in FIG. 4C, the apertures 184, 186, and 188 may be arranged on their respective membranes 170a, 170b, and 170c such that the apertures do not overlap when the membranes 170a, 170b, and 170c are stacked in the lower cannula housing 106. In certain embodiments, the apertures 184, 186, and 188 may be arranged on their respective membranes 170a, 170b, and 170c such that the apertures partially overlap when the membranes 170a, 170b, and 170c are stacked in the lower cannula housing 106. As described above, differential pressure of the insufflation gas over atmospheric pressure presses the membranes against each other. The slit 186 in membrane 170b is assisted in remaining closed by being sandwiched between membranes 170a and 170c.

Figure 5:
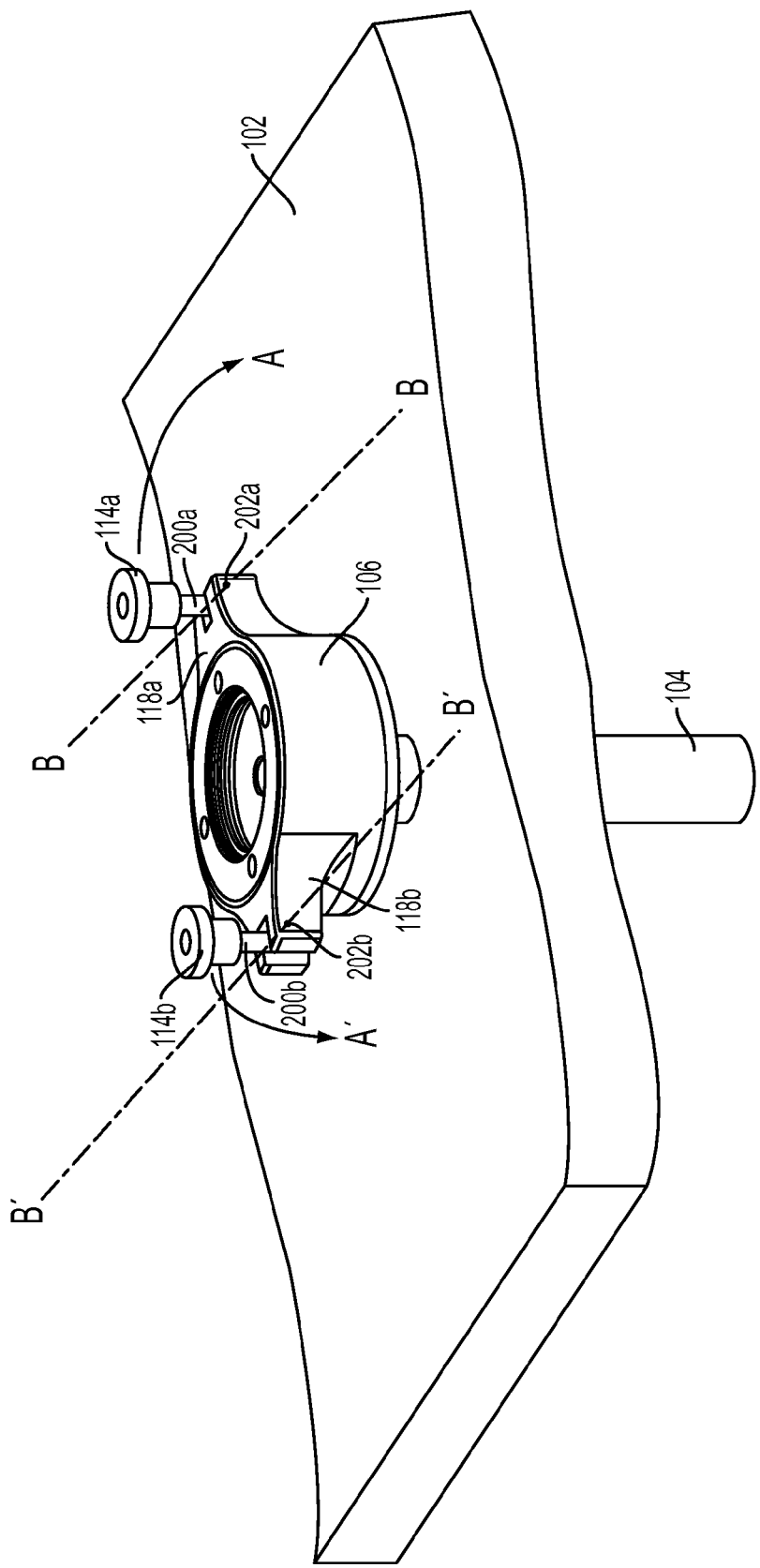
FIG. 5 is a perspective view of a cannula housing positioned in tissue according to an embodiment of the present invention.
Figure 6A:
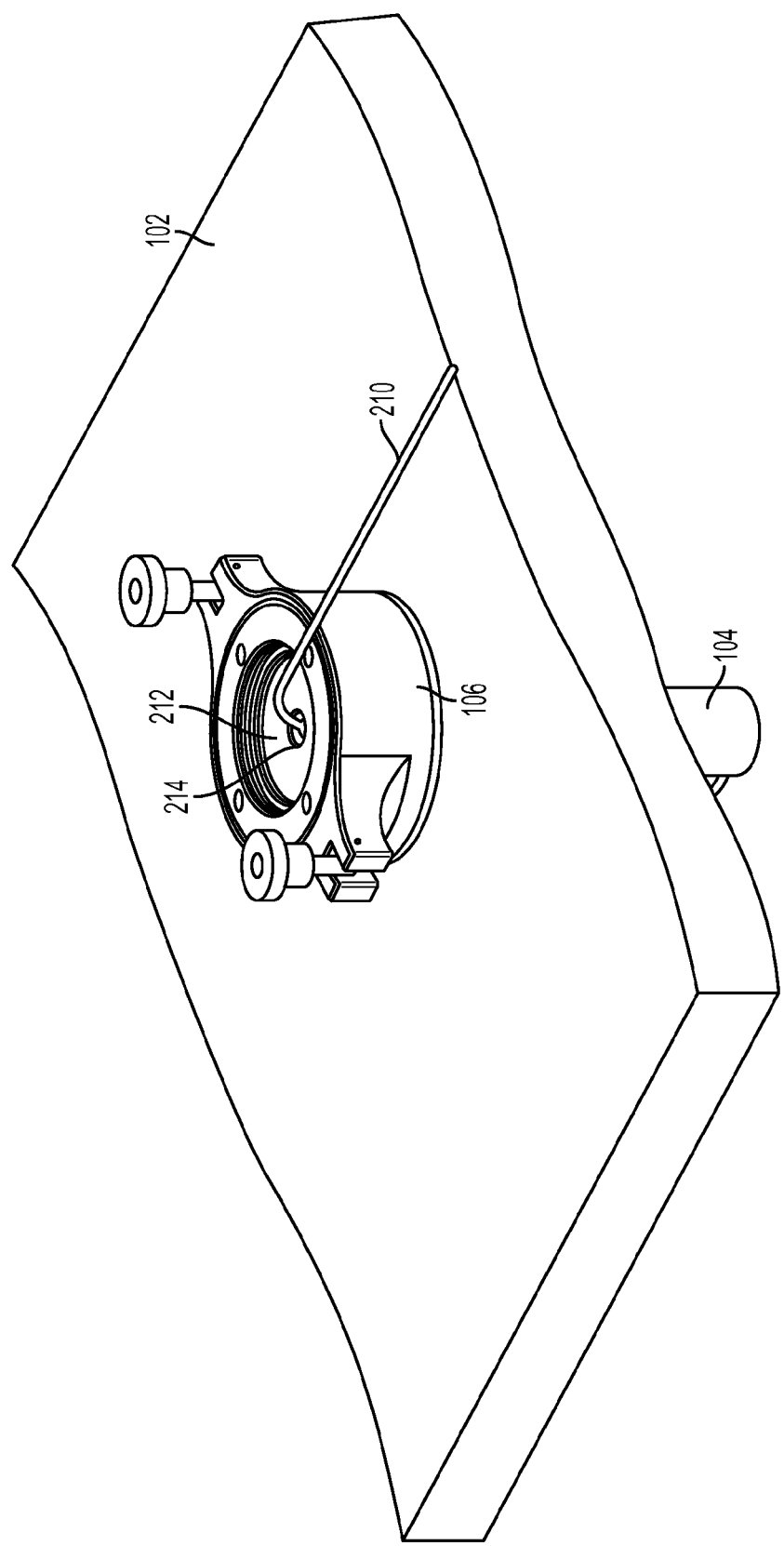
FIG. 6A is a perspective view of a cannula housing according to an embodiment of the present invention with a tether disposed therethrough.
Figure 6B:
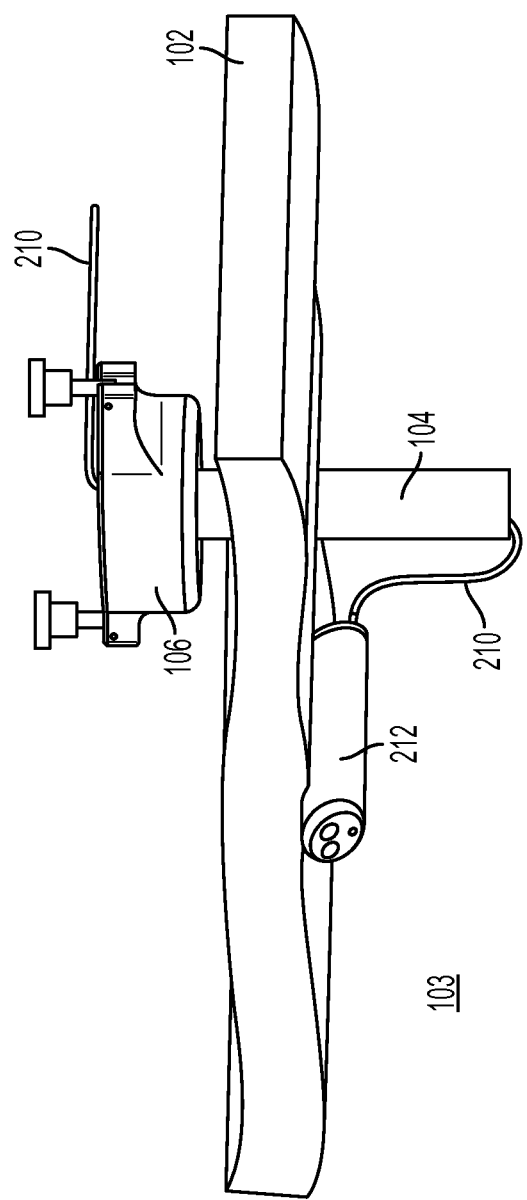
FIG. 6B is a perspective view of the cannula housing of FIG. 6A showing a camera in an internal site of a patient attached to the tether.

FIG. 5 shows a cannula tube 104 inserted through tissue 102 with membranes, such as any of the membranes described above in FIGS. 2A-4C, installed in the lower cannula housing 106. FIGS. 6A-B show a magnetic camera 212 placed in the abdominal cavity 103 through the lower cannula housing 106 and the cannula tube 104. The camera 212 may be attached to a tether 210. The tether includes one or more strands, for example, one strand may carry power to the camera, another strand carries image data from the camera, and another strand possibly carries gases or fluids to ports attached to the camera. The tether 210 runs from the camera 212 through the cannula tube 104 and the lower cannula housing 106. The tether 210 also passes through apertures 214 in membranes 212, such as, for example, the membranes 124a-b, 150a-c, and 170a-c described above. FIGS. 5 and 6A-B also show thumb screws 114a and 114b mounted on respective posts 200a and 200b. The posts 200a and 200b include threaded ends (not shown) onto which the thumb screws 114a and 114b are mounted. The posts 200a and 200b are connected to respective buttresses 118a and 118b by pins 202a and 202b. When the thumb screws are in a loose position, the thumb screws 114a and 114b may be rotated about pins 202a and 202b in the direction of arrows labeled "A" and "A'" about axes of rotation "B-B" and "B'-B'", respectively, in FIG. 5, to be out of the way of the upper cannula housing 108 being placed on top of the lower cannula housing 106. After the upper cannula housing 108 is placed on top of the lower cannula housing 106, the thumb screws 114a and 114b may be rotated in directions opposite to arrows "A" and "A'". Then, the thumb screws 114a and 114b may be turned on their respective posts 200a and 200b such the thumb screws 114a and 114b clamp down on respective buttresses 109a and 109b of the upper cannula housing 108.

Figure 7:
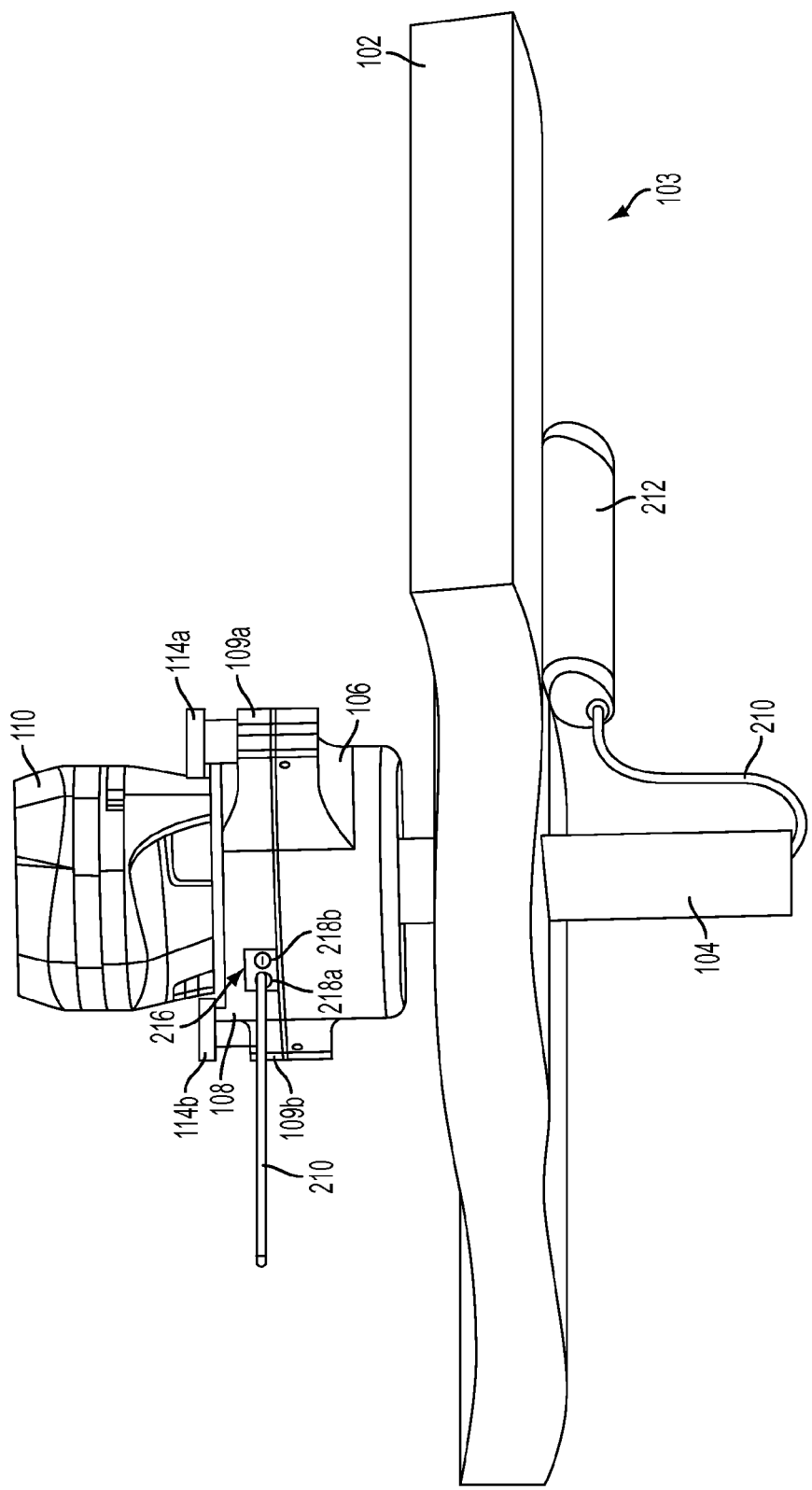
FIG. 7 is an embodiment of a cannula and trocar assembly according to an embodiment of the present invention showing a tether passing through a port on the cannula housing and an internally positioned camera.

FIG. 7 shows the upper cannula housing 108 and the cannula head 110 mounted on top of the lower cannula housing 106. The upper cannula housing 108 includes a port housing 216 that includes one or more ports 218a and 218b. The ports 218a and 218b provide a path for the tether 210 to exit the cannula tube 104 and the cannula housing 106, 108. The number of ports may correspond to the number of strands making up the tether 210, wherein each strand may pass through a distinct port. The ports 218a and 218b are sized to accommodate the tether 210. The ports 218a and 218b may be sized such that the tether 210 fits snugly therethrough or the ports 218a and 218b may include an additional gasket through which the tether 210 runs. For example, the gasket may be a compliant membrane that covers a port, such as, for example, port 218a, and the compliant membrane may include an aperture through which the tether may pass. The gasket also may be an o-ring positioned within a port, such as, for example, port 218a, that snugly fits with a tether passing therethrough. The snug fit of the gasket further retards leakage of insufflation gases. When the tether 210 is drawn through the ports 218a and 218b, the tether 210 is biased to a side of the cannula tube 104, i.e., away from the center of the cannula tube 104 nearest to the ports 218a and 218b. Consequently, the tether 210 is out of the way of any additional endoscopic tools passing through the cannula tube 104.

Figure 8:
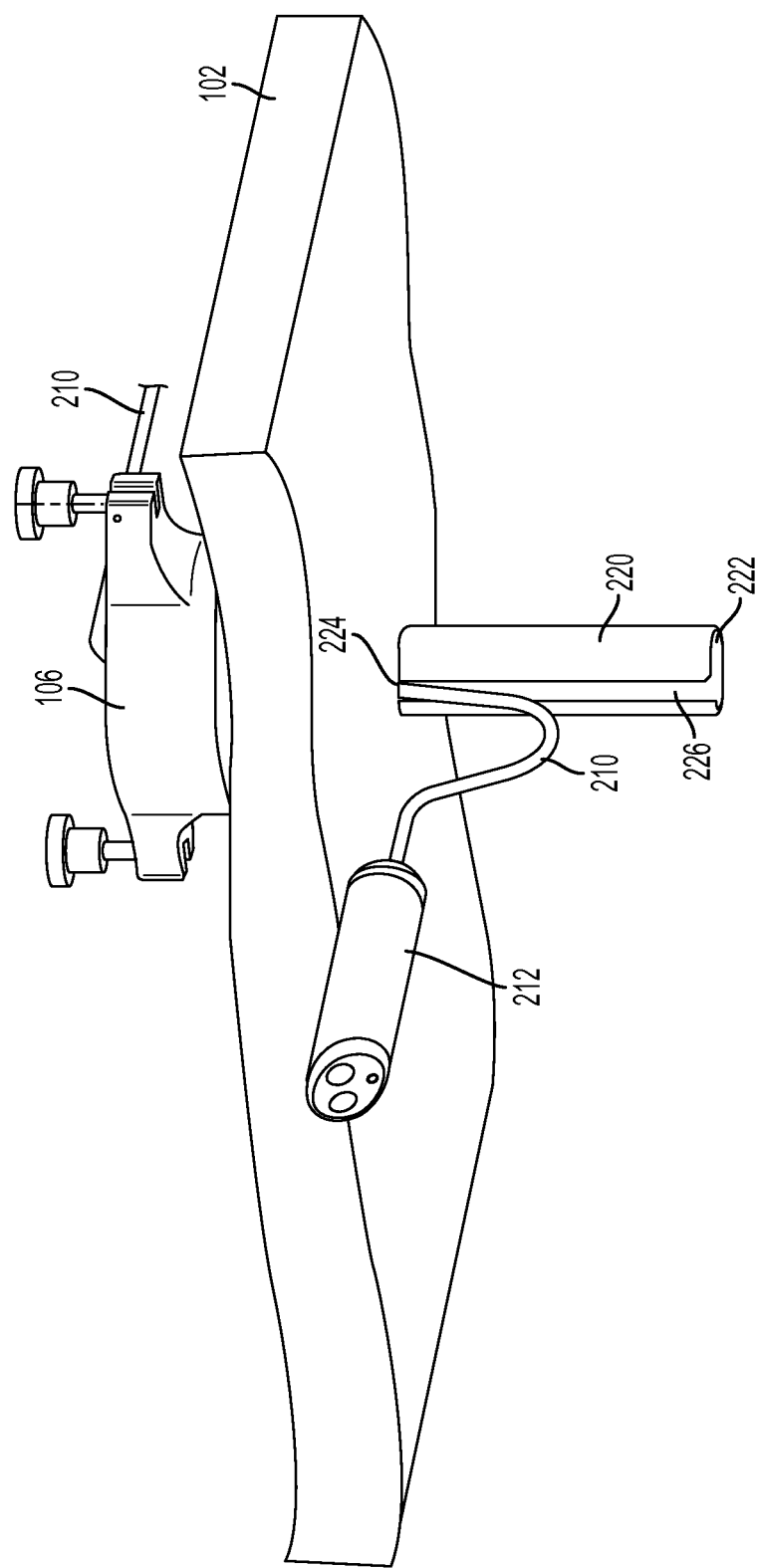
FIG. 8 is an embodiment of a cannula and tethered housing from the perspective of an internal site of the patient.

FIG. 8 shows another embodiment of a cannula tube 220 having a slot 226 defining an opening running along the length of the cannula tube 220, generally, and preferably substantially parallel to its longitudinal axis. The slot 226 enables the tether 220 to exit the cannula tube 220 at a more proximal point 224 than the distal end 222 of the cannula tube 220. Removing the tether 210 from the cannula tube 220 at the more proximal point 224 minimizes interactions between the tether 210 and other endoscopic devices (not shown) in the cannula tube 220, which may cause tugging on the tether 210 (and inadvertent movement of the camera 212) or cause inadvertent movement of endoscopic tools.

In various embodiments, the cannula housing may be structured for movement to reposition the openings to the passage. For example, FIGS. 9A-9I show an embodiment of a cannula including a bracket 230 and a rotating housing 233. The rotating housing 233 includes a passage 276 (FIG. 9B) that is in fluid communication with a bracket opening 270 (FIG. 9D) in the bracket 230. The rotating housing 233 may also include a first opening 272 and a second opening 274, each of which can be in fluid communication with the passage 276. The first opening 272 may include first membranes 236 and respective apertures 238. The second opening 274 may include second membranes 244 and respective apertures 246. In certain embodiments, the first membranes 236 and the second membranes 244 can include a plurality of membranes, similar to the membranes shown in FIGS. 2A-4E. The apertures 238 and 246 can be in fluid communication with the passage 276. The bracket 230 may be coupled to a hollow cannula tube 220 and the bracket opening 270 may be in fluid communication with the cannula tube 220. The cannula tube 220 may include a longitudinal slot 226. Alternatively, the cannula tube 220 can be similar to those shown above with respect to FIGS. 1A-7, for example. The rotating housing 233 is rotationally coupled to the cannula bracket 230 by bearings 240. The bearings 240 may be any type of bearings, such as ball bearings, planar bearings, and/or journal bearings, for example.

A seal housing 260 can be positioned intermediate the bracket 230 and the rotating housing 233. Referring particularly to FIG. 9E, the seal housing 260 can include an interior surface 262 that includes a slightly larger profile than an exterior cylindrical surface of the rotating housing 233. The seal housing 260 also includes a seal passage 266 in fluid communication with the bracket opening 270 and the passage 276 in the rotating housing 233. When assembled, the close fit between the rotating housing 233 and the seal housing 260 provides a seal for the passage 276 and/or the first and second openings 272 and 274 that can inhibit the escape of gases. For example, in use, insufflation gases in a patient's abdomen can be inhibited from escaping through the cannula tube 220 and the passage 276 by the interior surface 262 of the seal housing 260. The interior surface 262 of the seal housing 260 can also inhibit the escape of insufflation gases through the first opening 272 when the rotating housing 233 is rotated such that the first opening 272 is aligned with a portion of the interior surface 262, an example of which is illustrated in FIG. 9H. The interior surface 262 of the seal housing 260 can also inhibit the escape of insufflation gases through the second opening 274 when the rotating housing 233 is rotated such that the second opening 274 is aligned with a portion of the interior surface 262, an example of which is illustrated in FIG. 9D.

Referring to FIG. 9H, the aperture 238 is shown as a slit that is aligned with a slit 264 in the seal housing 260. The slit 264 in the seal housing 260 can accommodate the tether 210 of the camera. In certain embodiments, the aperture 238 may not be aligned with the slit 264 in the seal housing 260 to further inhibit the escape of insufflation gases. For example, if the aperture 238 is a slit, such as the slit shown in FIG. 9H, then the aperture 238 may be rotated ninety degrees relative to the slit 264 in the seal housing 260. As another example, if the aperture 238 is a circular hole, then the hole may be offset from the slit 264 in the seal housing 260.

Figure 9A:
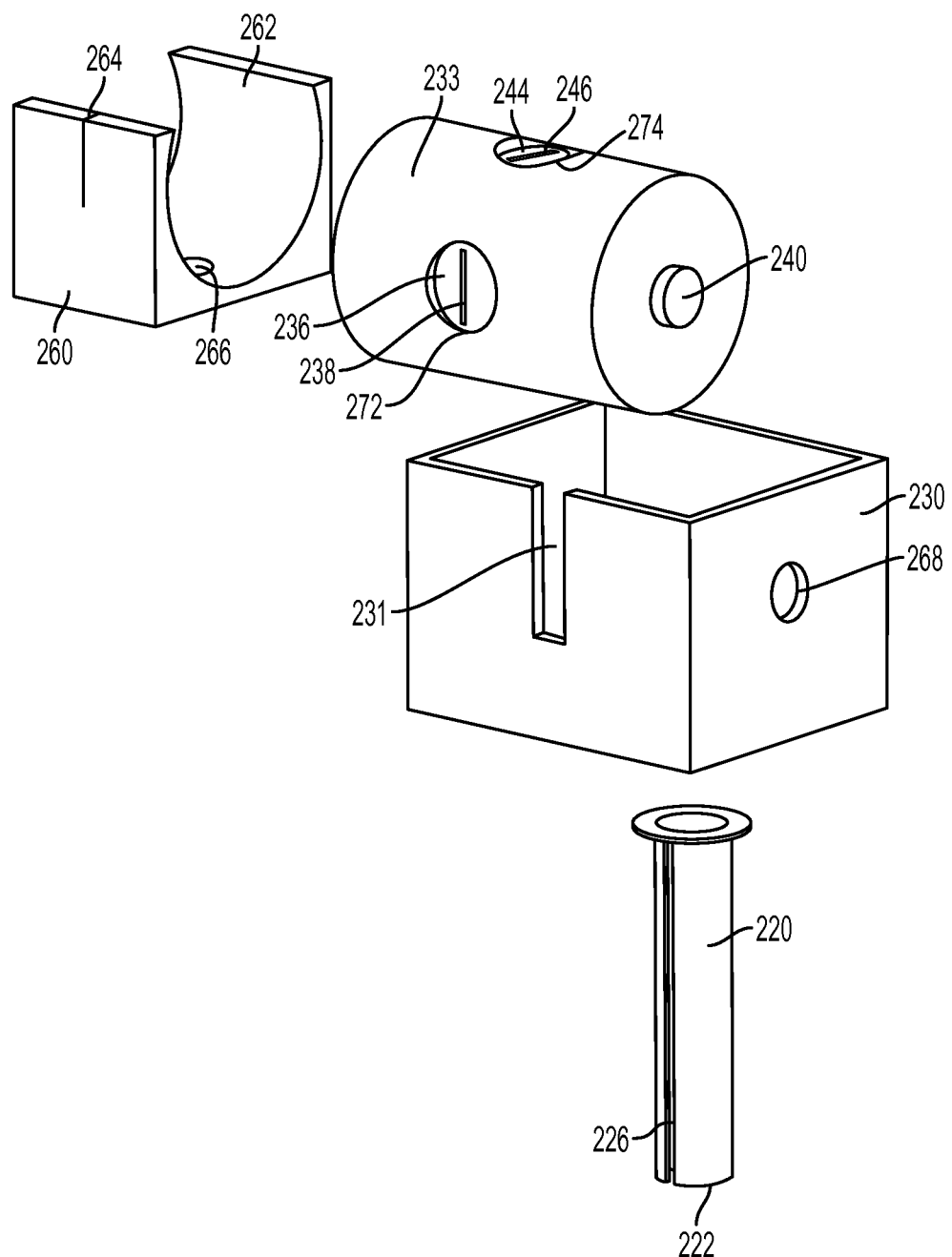
FIG. 9A is a front exploded view of a cannula tube and housing according to an alternative embodiment of the present invention.
Figure 9B:
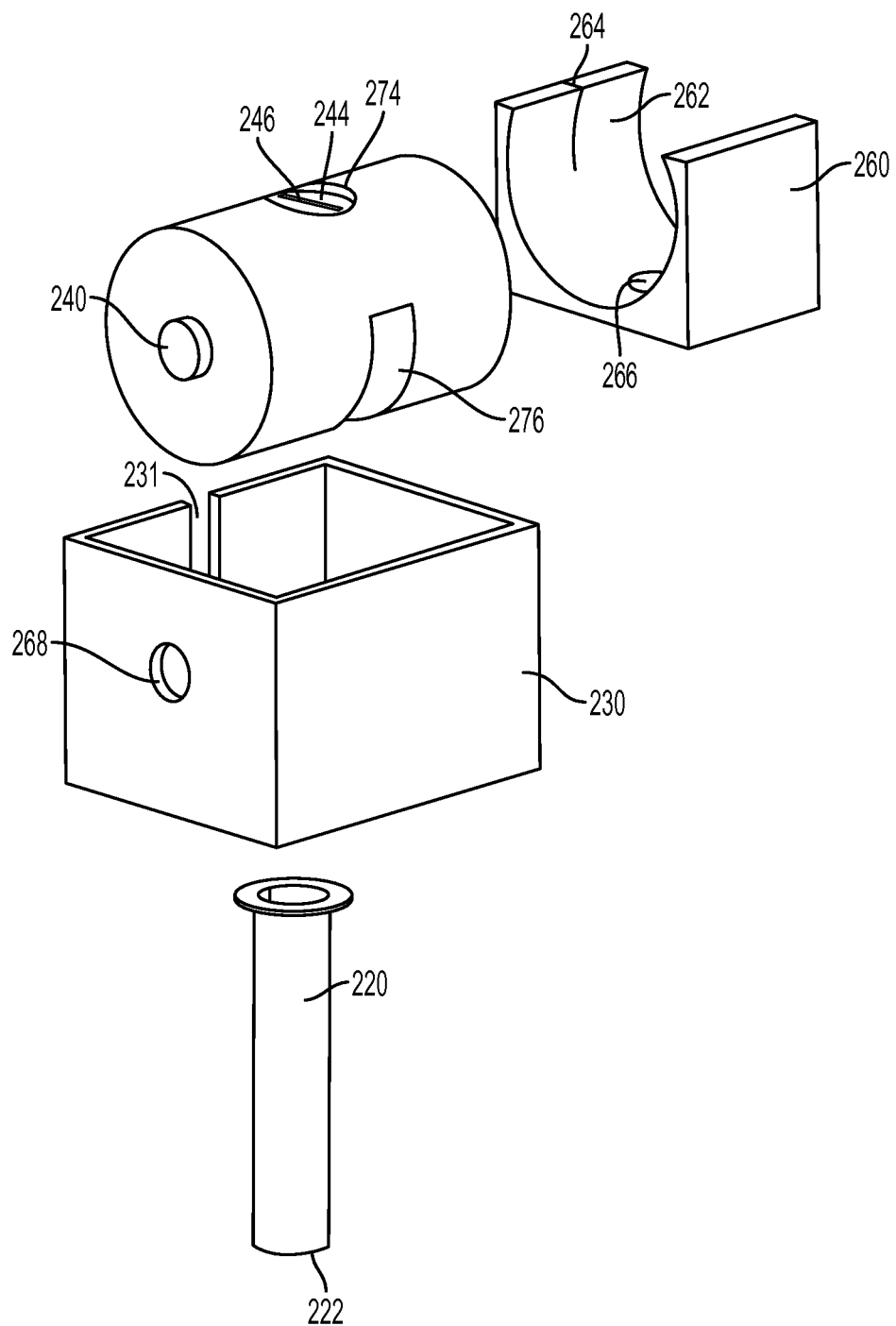
FIG. 9B is a rear exploded view of the cannula tube and housing of FIG. 9A.
Figure 9C:
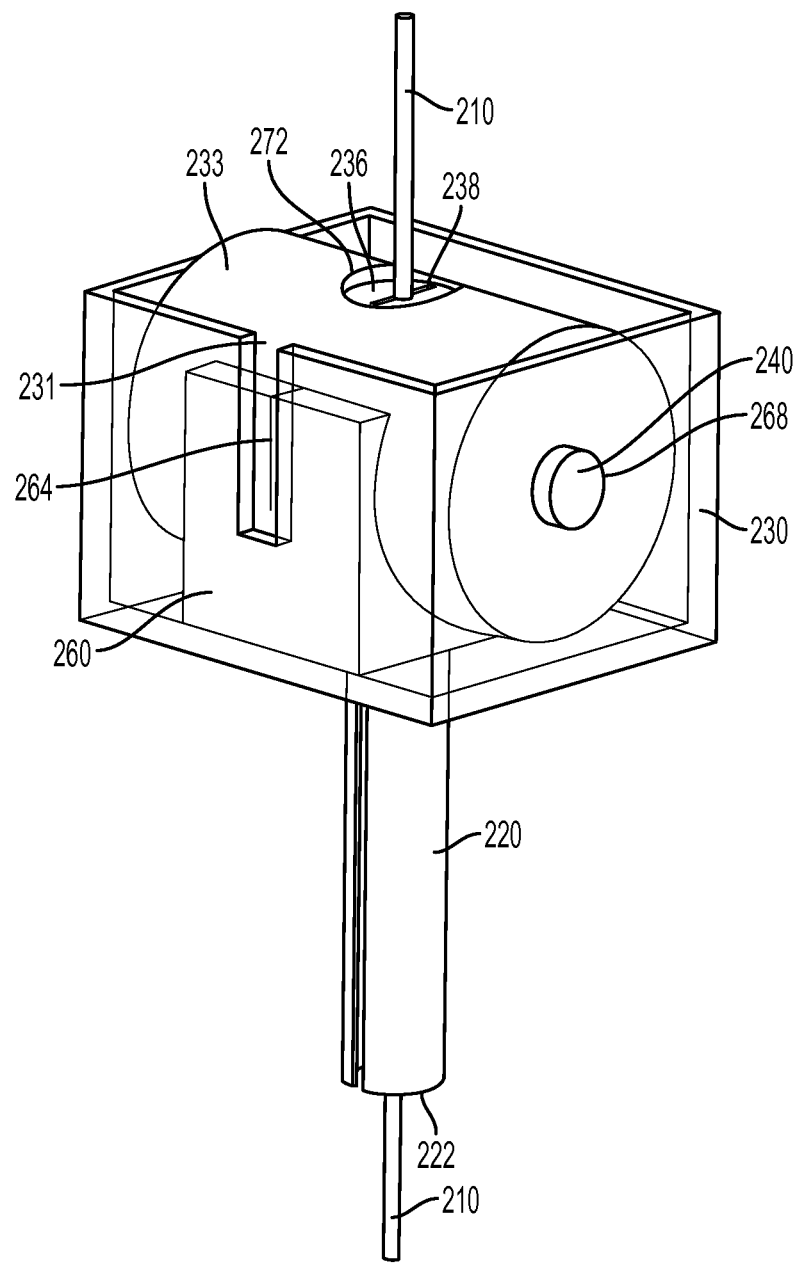
FIG. 9C is a front perspective view of the cannula tube and housing of FIG. 9A with a tether passing therethrough, wherein the bracket is shown as clear for visibility of the housing.
Figure 9D:
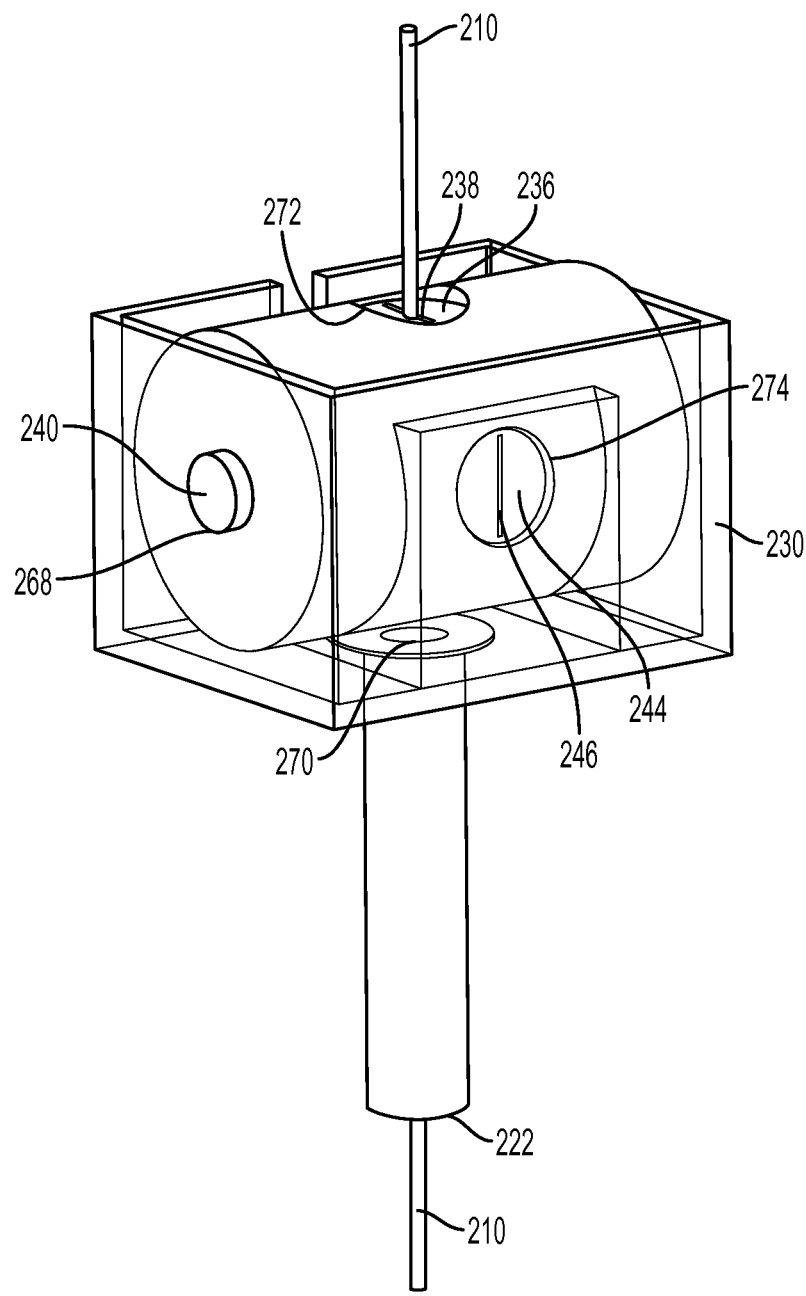
FIG. 9D is a rear perspective view of the cannula tube and housing of FIG. 9A with the tether passing therethrough, wherein the bracket is shown as clear for visibility of the housing.
Figure 9E:
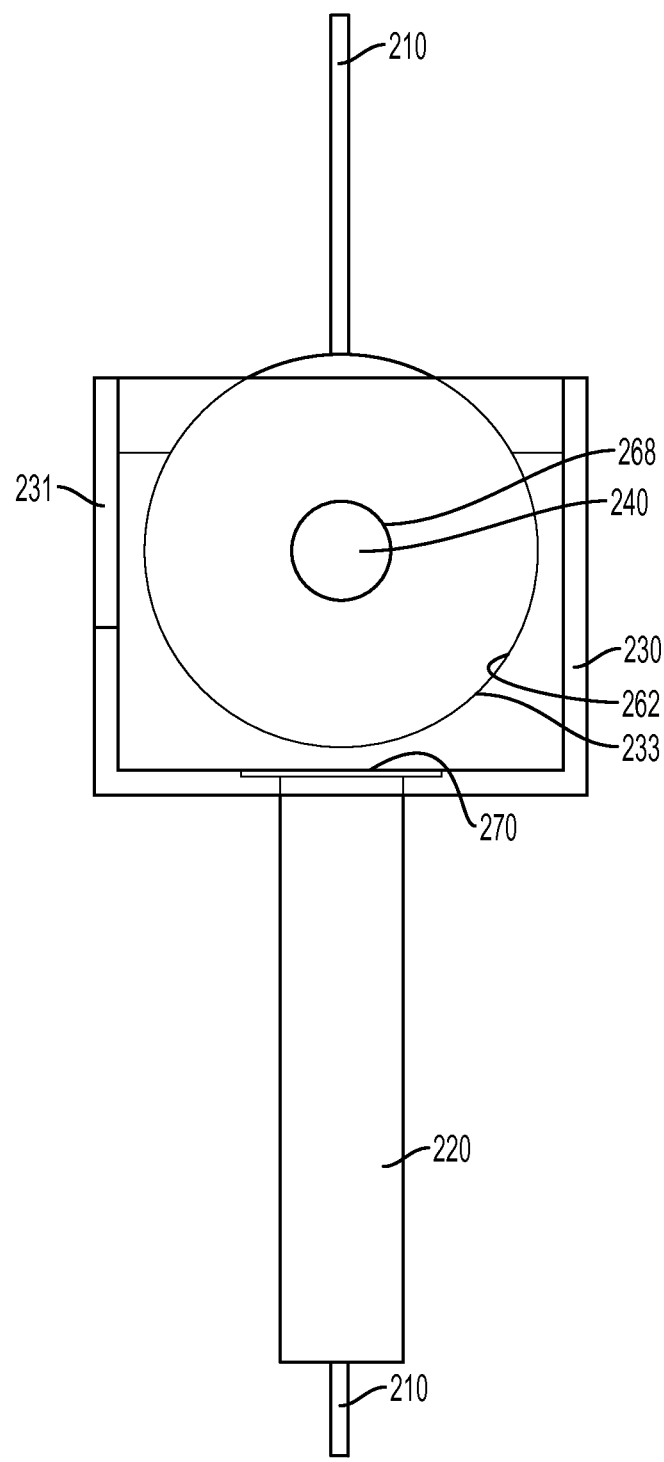
FIG. 9E is a side view of the cannula tube and housing of FIG. 9A with the tether passing therethrough, wherein the bracket is shown as clear for visibility of the housing.
Figure 9F:
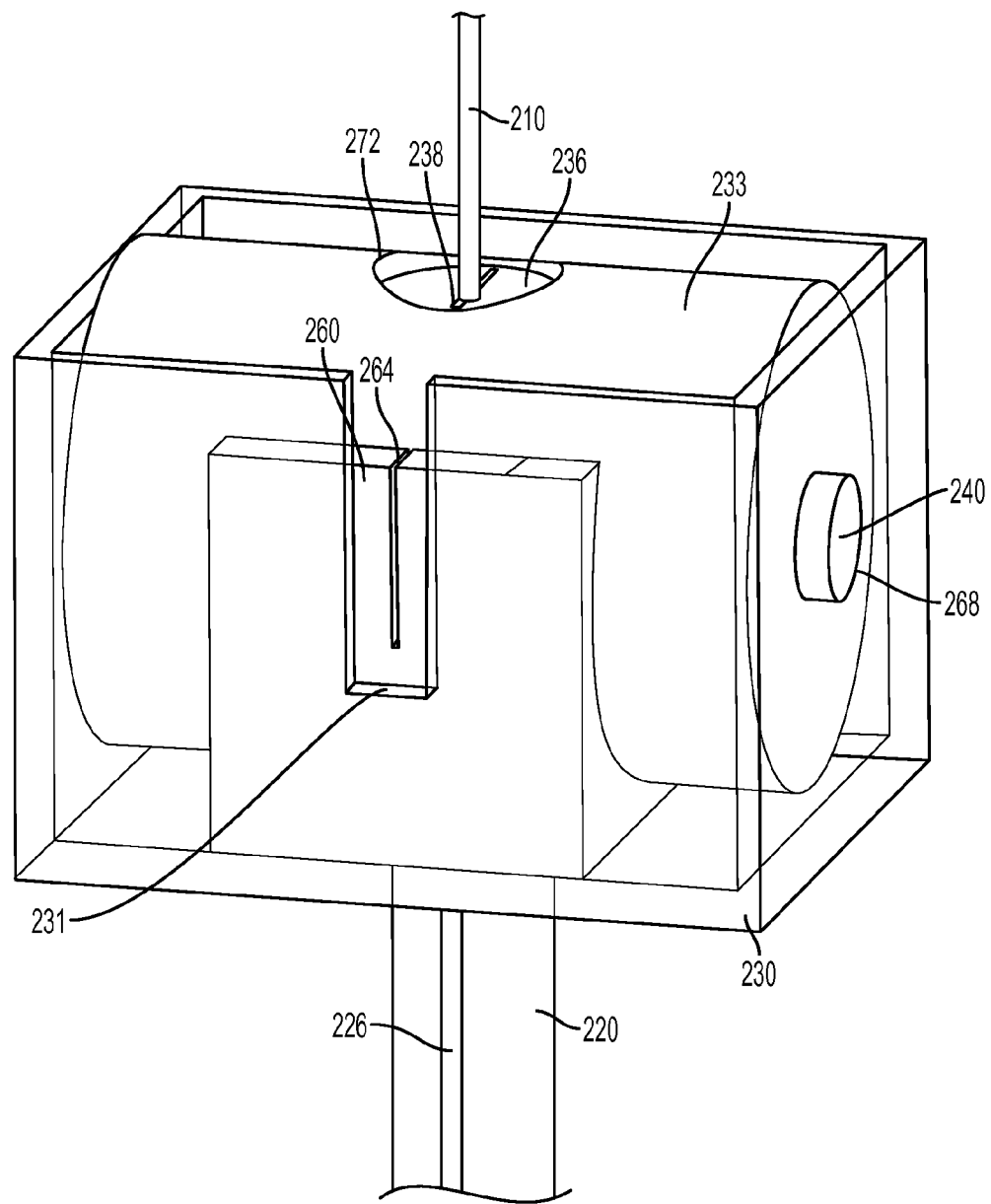
FIG. 9F is a front perspective view of the cannula tube and housing of FIG. 9A with the tether passing therethrough, wherein the bracket is shown as clear for visibility of the housing.

Referring to FIG. 9C, in use, the rotating housing 233 can be oriented such that the first opening 272 is aligned with a longitudinal axis of the cannula tube 220 and the bracket opening 270. An obturator shaft and tip, such as obturator shaft 115 and obturator tip 116, shown in FIG. 1A, may be inserted through the first opening 272 and the apertures 238 in the membranes 236 therein such that the obturator top 116 protrudes from the distal end of the cannula tube 220. An obturator grip, such as obturator grip 112, may be attached to a proximal end of the obturator shaft 115, and may couple to the cannula housing 233 and/or the bracket 230. The obturator tip 116 may guide the cannula tube 220 through an otomy in a patient. Then, the obturator shaft 115 and obturator tip 116 can be removed from the cannula tube 220, bracket 230, and rotating housing 233. As illustrated in FIG. 9I, the close spacing between the seal housing 260 and the rotating housing 233 can inhibit the escape of insufflation gases through the passage 276 in the rotating housing. A camera can be passed through the apertures 238 in the first membranes 236 and through the cannula tube 220 and into a body cavity. Referring to FIGS. 9C-9F, a tether 210 of the camera is shown passing through the first apertures 238 and out through the cannula tube 220.

Figure 9G:
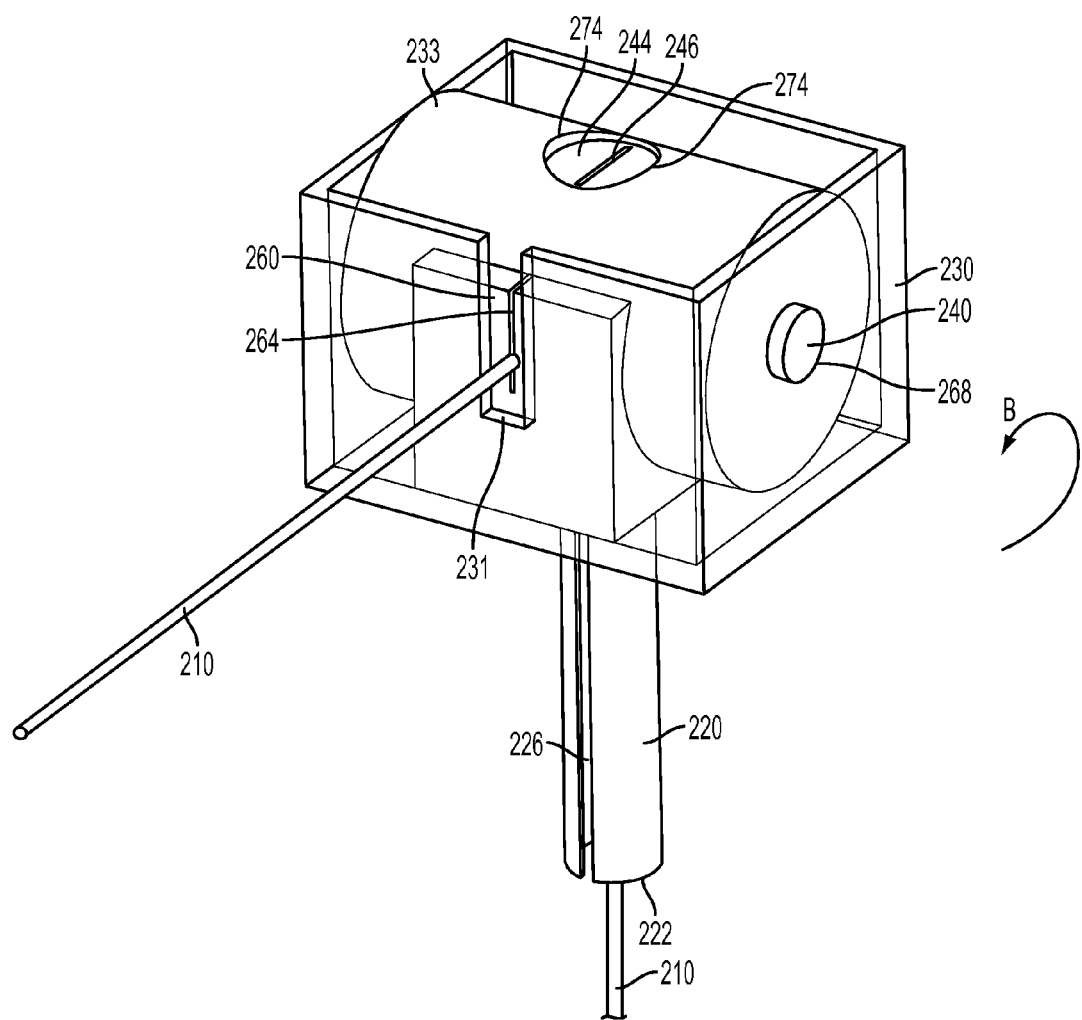
FIG. 9G is a perspective view of the cannula tube and housing of FIG. 9F with the tether passing therethrough, wherein the housing is moved to a rotated positioned.
Figure 9H:
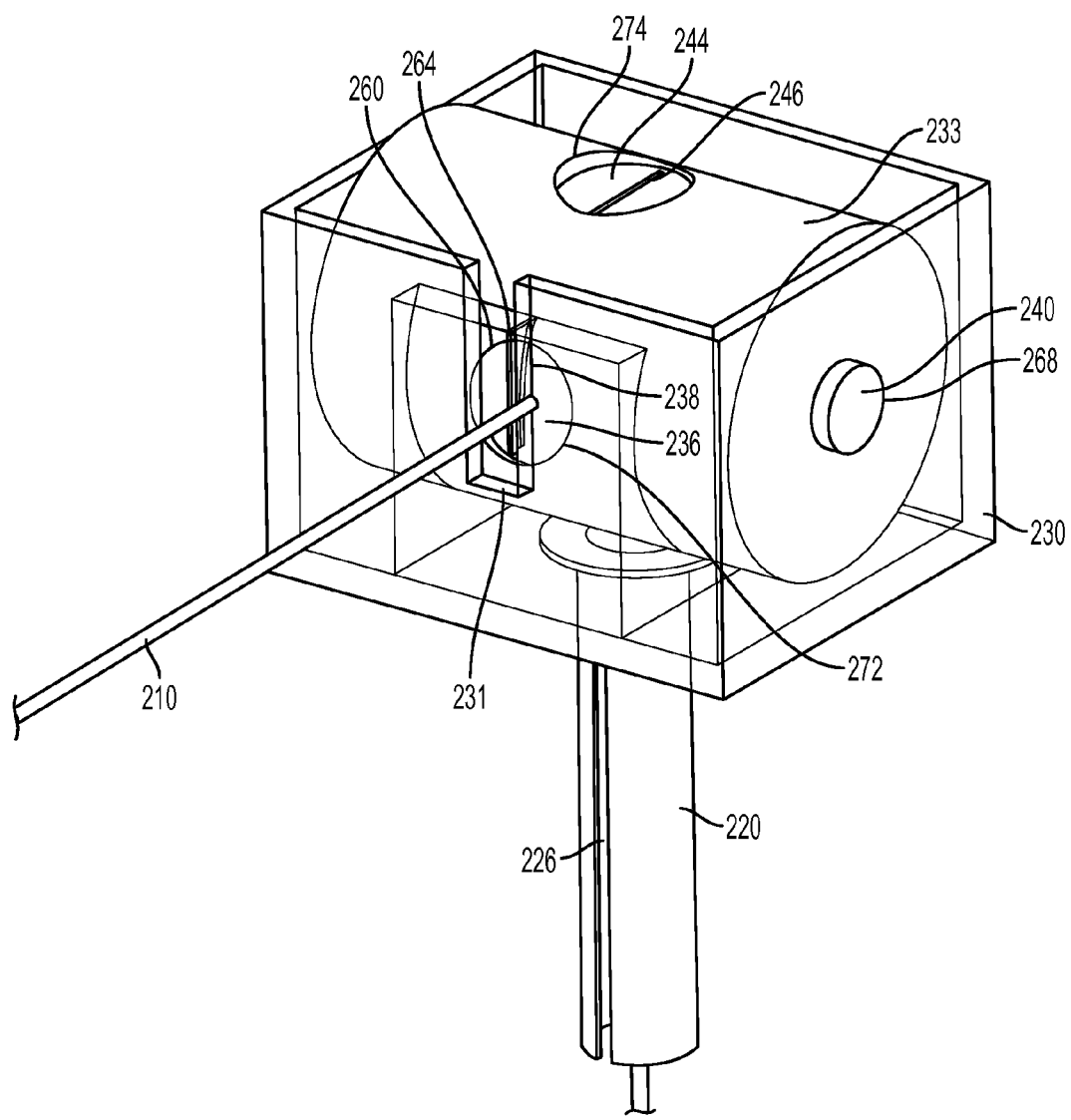
FIG. 9H is a second perspective view of the cannula tube and housing of FIG. 9F with the tether passing therethrough, wherein the housing is moved to a rotated positioned.
Figure 9I:
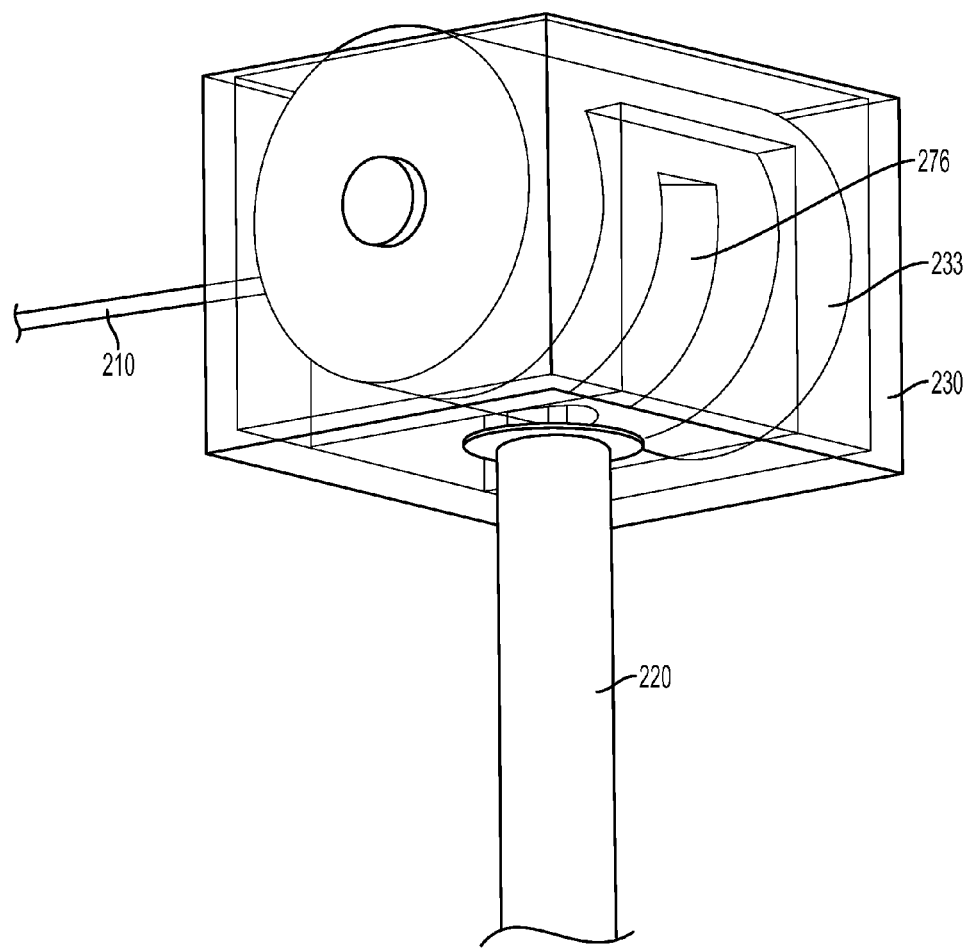
FIG. 9I is a third perspective view of the cannula tube and housing of FIG. 9H with the tether passing therethrough, wherein the housing is moved to a rotated positioned.

Referring to FIG. 9G, after the camera is positioned in the body cavity and the tether 210 passes through the cannula tube 220 and the first opening 272 in the rotating housing 233, the rotating housing 233 can be rotated in the direction of arrow B. In the rotated configuration, the first opening 272 is not aligned with the longitudinal axis of the cannula tube 220. As a result, the tether 210 is biased toward a perimeter of the cannula tube 220. If the cannula tube 220 includes a longitudinal slot 226, then it can be advantageous for the tether 210 to be biased toward a side of the cannula tube 220 on which the longitudinal slot 226 is located. With the tether 210 biased towards the perimeter of the cannula tube 220, additional surgical instruments can be inserted through the apertures 246 in the second membranes 244 and the cannula tube 220 while minimizing interference between the tether 210 and the surgical instrument. Any interference can cause tugging of the tether, which may cause undesired movement of the camera in the patient. Any interference can also cause unwanted movement of the surgical instrument. In the rotated configuration, the first opening 272 is adjacent to the interior surface 262 of the seal housing 260. The slit 264 or similar opening in the seal housing 260 can accommodate the tether 210 of the camera as shown in FIGS. 9G and 9H.

Figure 10A:
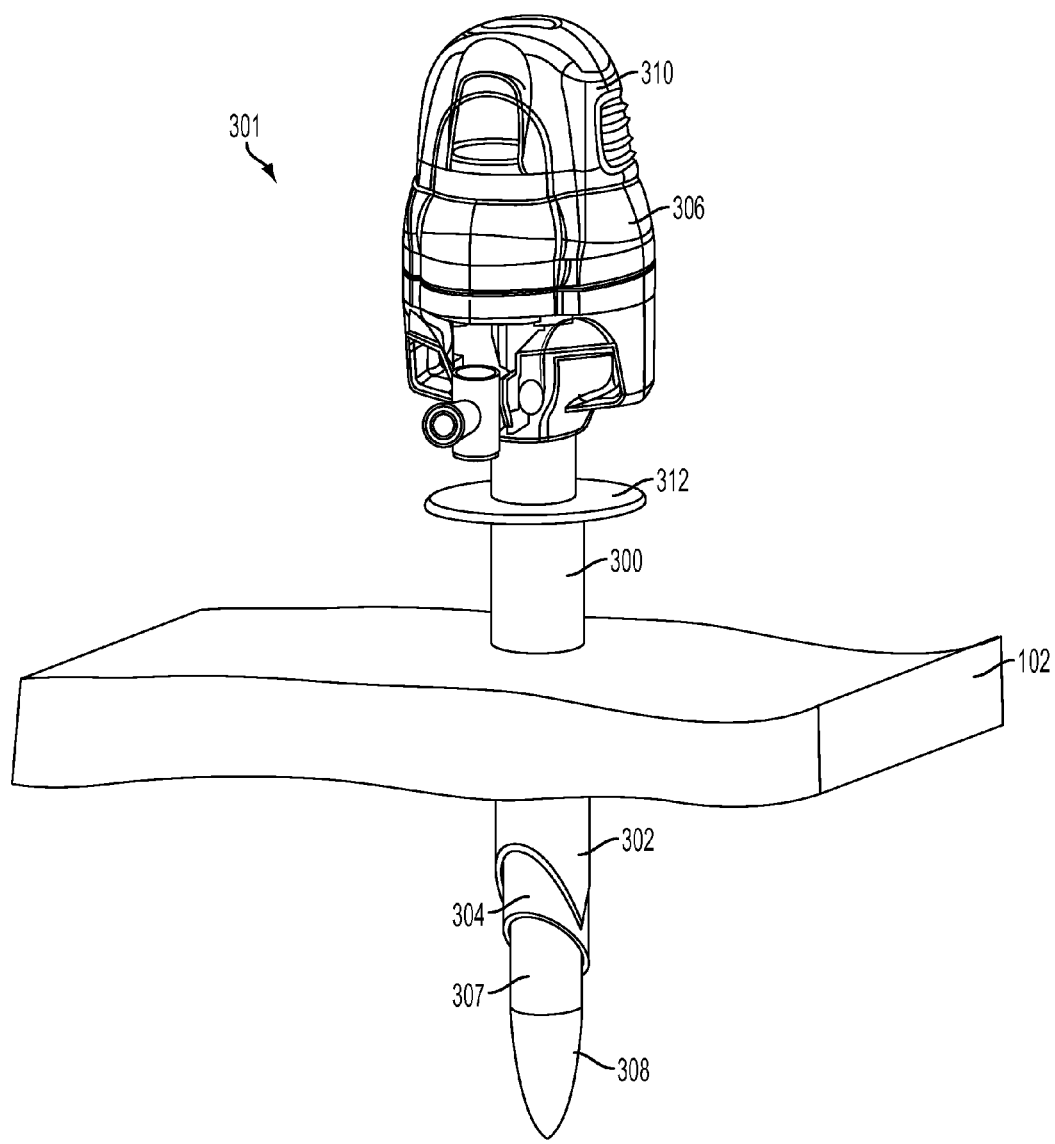
FIG. 10A is a perspective view of a trocar and obturator assembly according to an embodiment of the present invention.

In various embodiments, a cannula sleeve may be provided for enhanced sealing. Referring to FIG. 10A, a perspective view of another embodiment of a trocar assembly 301 passing through a cannula sleeve is shown. The trocar assembly 301 includes a cannula head 306 attached to a cannula tube 304. An obturator shaft 307 and obturator tip 308 are attached to an obturator grip 310, and the obturator shaft 307 and obturator grip 308 pass through the cannula head 306 and cannula tube 304. A cannula sleeve 300 surrounds or encases the cannula tube 304. The cannula sleeve 300 includes a seal 302 at its distal end. When the trocar assembly 301 penetrates tissue 102, the cannula sleeve 300 also penetrates the tissue 102.

Figure 10B:
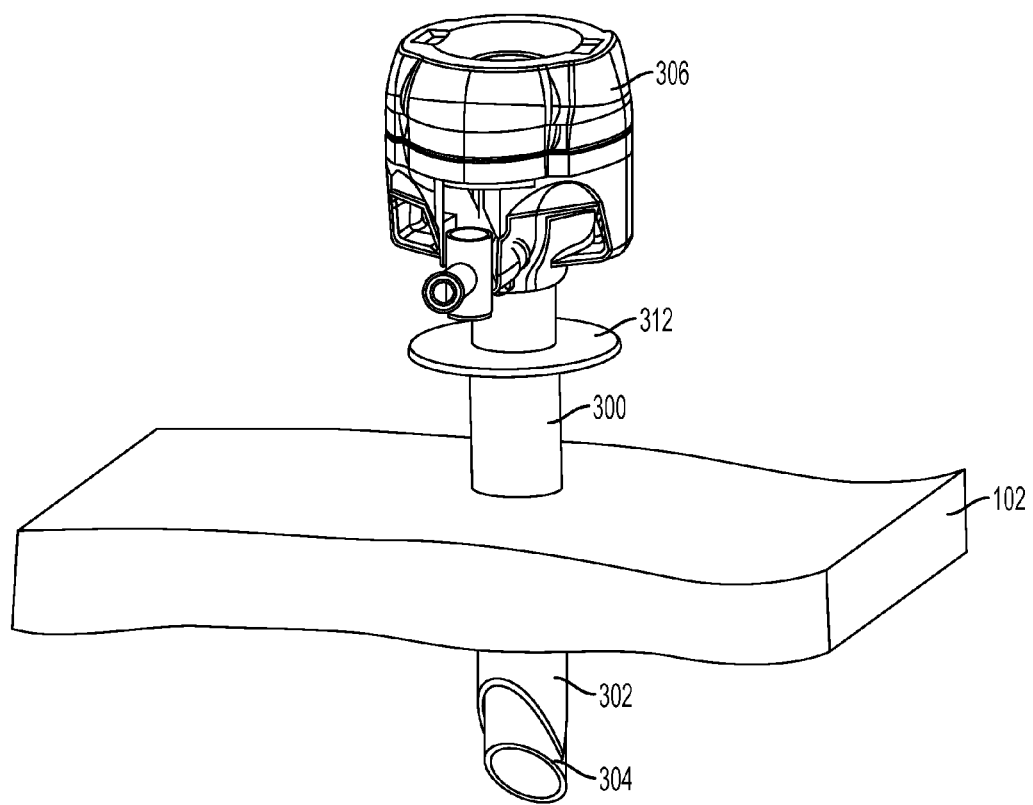
FIG. 10B is a perspective view of the trocar assembly of FIG. 10A wherein an obturator assembly is removed.
Figure 10C:
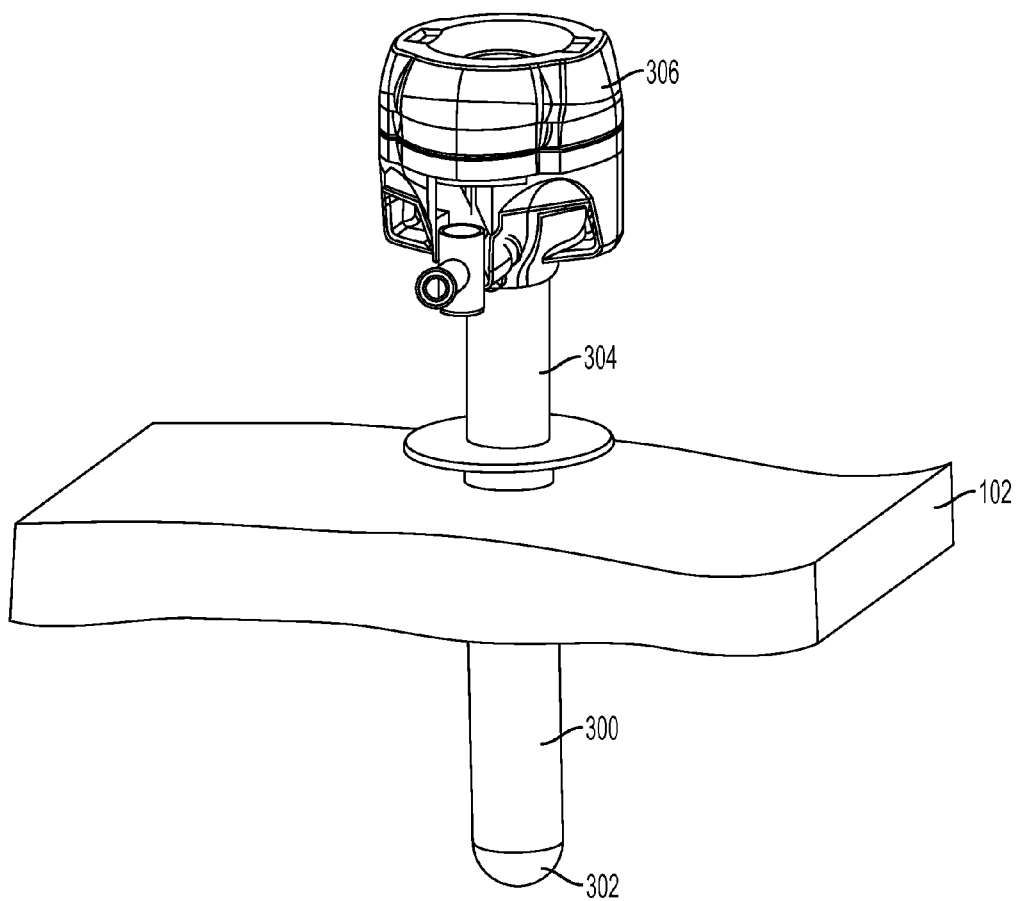
FIG. 10C is a perspective view of the trocar assembly of FIG. 10B wherein a cannula assembly is partially removed from an embodiment of a cannula sleeve, showing a seal on the sleeve in a closed position.
Figure 10D:
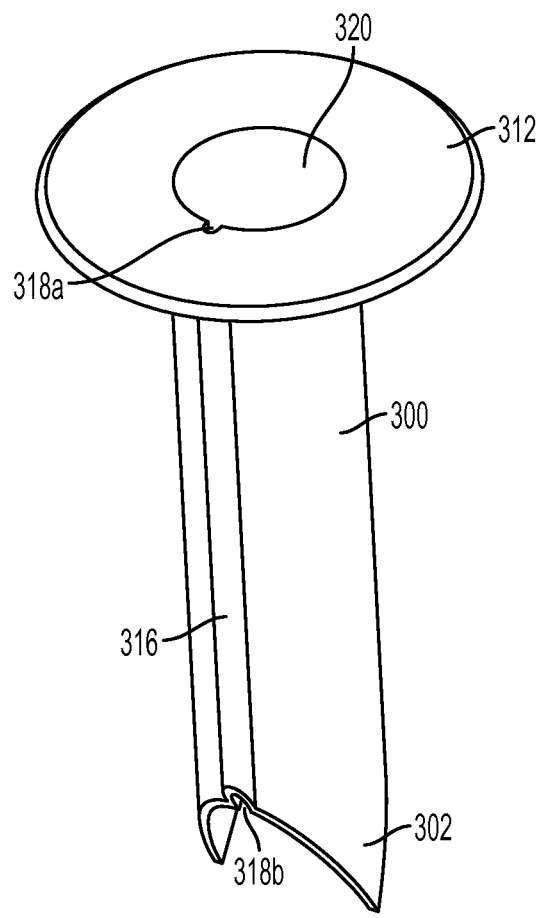
FIG. 10D is a perspective view of an embodiment of a cannula sleeve of the trocar assembly of FIG. 10A, showing the seal on the sleeve in an open position.
Figure 10E:
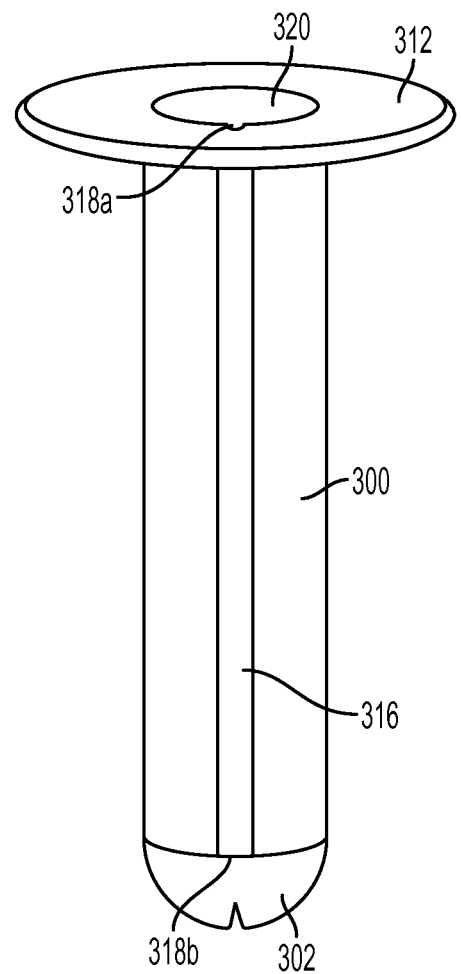
FIG. 10E is a perspective view of the cannula sleeve of FIG. 10D showing the seal on the sleeve in the closed position.
Figure 10F:
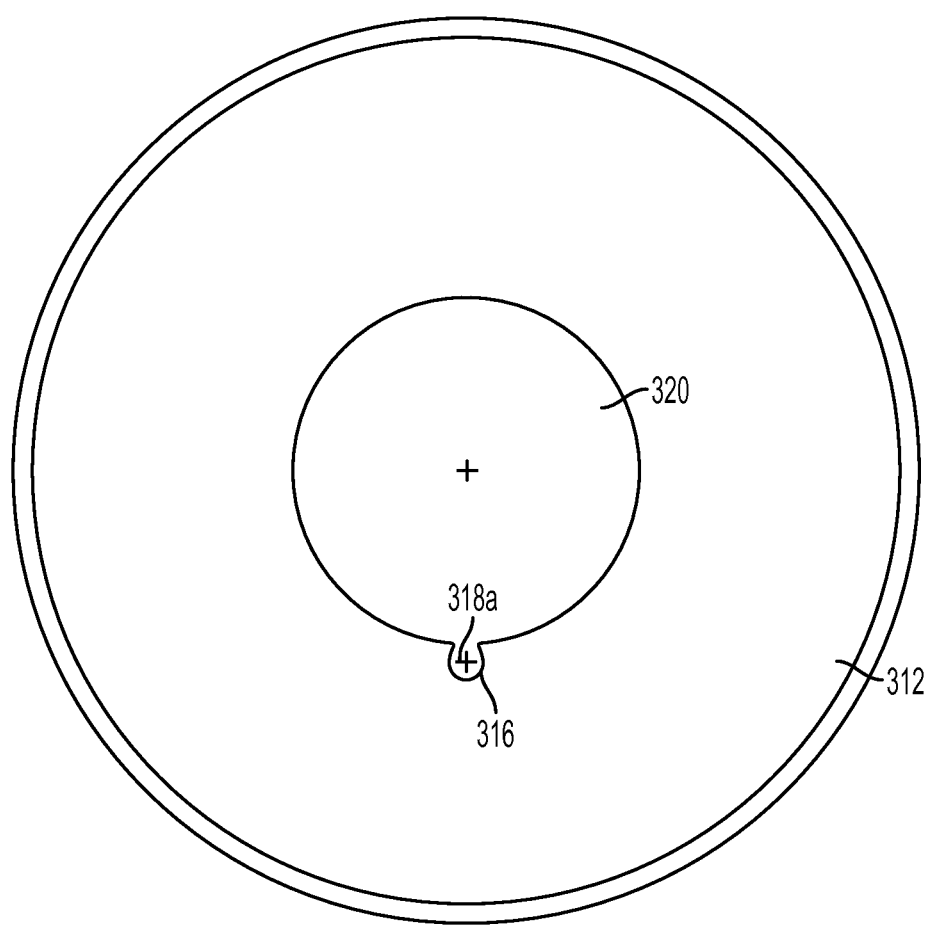
FIG. 10F is a top view of the cannula sleeve of FIG. 10D.

FIG. 10D shows the cannula sleeve 300 alone. The cannula sleeve 300 includes a sleeve seal 302 at its distal end. In FIG. 10D, the sleeve seal 302 is shown in its open configuration. The sleeve seal 302 preferably is biased in a closed position (as shown in FIG. 10E). The sleeve seal 302 may be a duckbill seal, a clamshell seal, or any other type of seal. The cannula sleeve 300 generally comprises a substantially rigid or semi-rigid material, such as, for example, plastic or stainless steel. The sleeve seal 302 comprises a compliant material, such as, for example, silicone or rubber. The sleeve seal 302 may be attached to the cannula sleeve 300 by, for example, overmolding, adhesives, fasteners, welding, or the like. The cannula sleeve 300 may include a sleeve flange 312. The sleeve flange 312 provides a surface that can stops the cannula sleeve 300 from accidentally passing completely through an otomy in tissue. The cannula sleeve 300 also includes a tether channel 316. As shown in FIGS. 10D and 10G, the tether channel 316 may be outside of the periphery of the cannula tube 300 but also is in fluid communication with the hollow interior of the cannula tube 300. The tether channel 316 may include an open end 318a at its proximal end and an open end 318b at its distal end. The tether channel 316 and the open ends 318a and 318b can receive a camera tether, enabling the camera tether to pass through the cannula sleeve 300 without intruding on the hollow interior of the cannula tube 300. The open end 318b at the distal end of the cannula tube 300 also enables a camera tether to bypass the sleeve seal 302. As shown in FIG. 10E, when the sleeve seal 302 is closed, the hollow interior of the cannula tube 300 substantially is not in fluid communication with a body cavity into which it is inserted. The open end 318 is outside of the sleeve seal 302 and enables the camera tether to bypass the sleeve seal 302.

In use, after the obturator shaft 307 and obturator tip 308, cannula tube 304, and sleeve seal 300 have been inserted through tissue 102, the obturator tip 308 and shaft 307 may be removed, as shown in FIG. 10B. The cannula tube 304 still extends through the cannula sleeve 300, and the sleeve seal 302 therefore remains open.

In FIG. 10C, the cannula tube 304 has been partially withdrawn from the tissue 102 and from the cannula sleeve 300. The cannula sleeve 300 remains inserted in the body cavity through the tissue 102. Because the cannula tube 304 has been withdrawn from the distal end of the cannula sleeve 300, the sleeve seal 302 is able to close. The closed sleeve seal 302 inhibits the escape of insufflation gases. As described above, the sleeve seal 302 may be biased in a closed position such that it closes in the absence of the cannula tube 304 or other endoscopic device passing through the cannula tube 304. Because the cannula sleeve 300 is made of a rigid or semi-rigid material, it maintains its shape (in other words, the cannula sleeve 300 does not collapse) when the cannula tube 304 is removed.

Figure 10H:
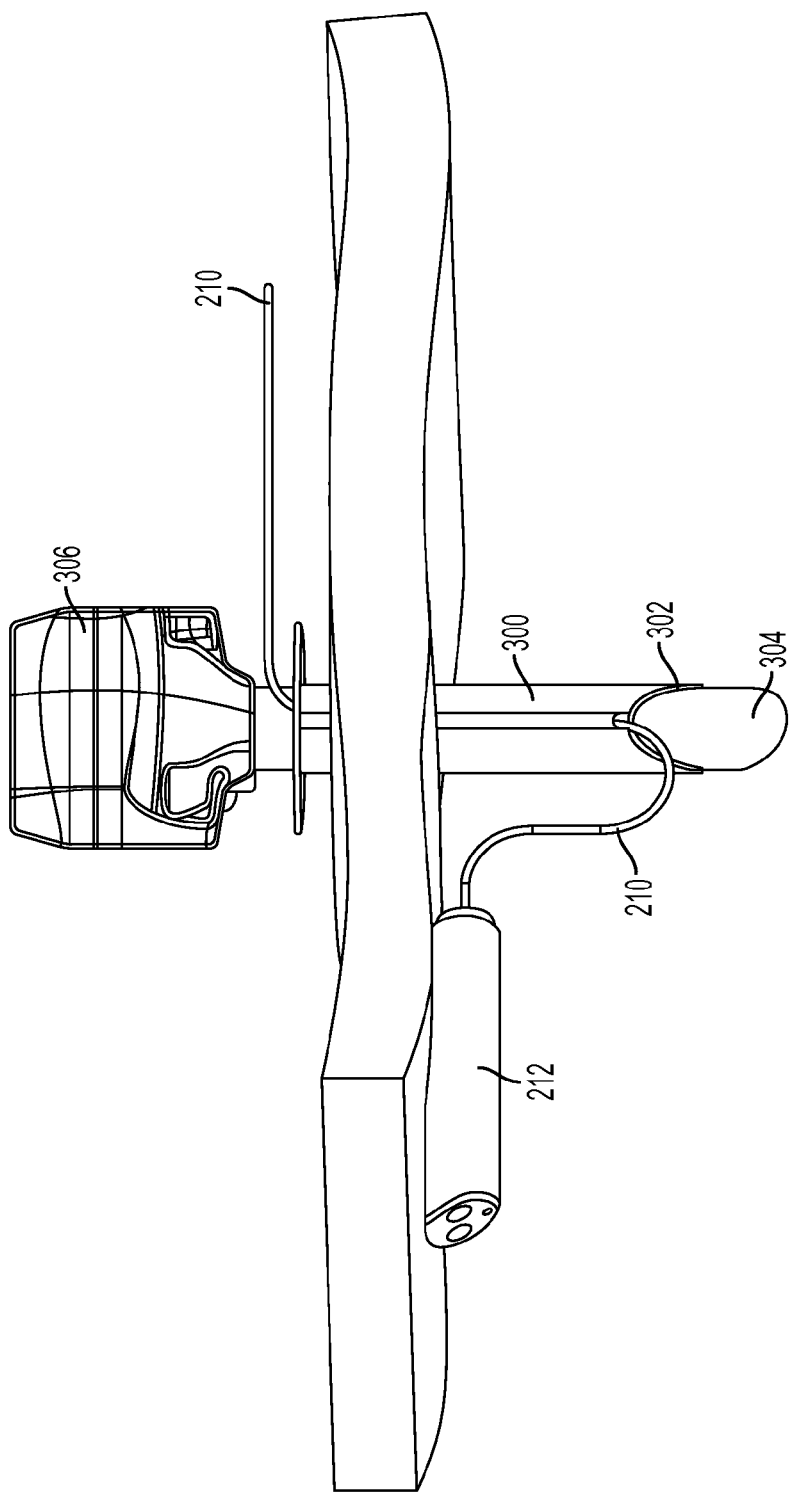
FIG. 10H is a perspective view of the trocar assembly of FIG. 10B with a camera and a tether.

FIG. 10H shows the cannula sleeve 300 with the camera 212 inserted therethrough. In addition, the cannula tube 304 has been reinserted into the cannula sleeve 300. Because the tether 210 is in the tether channel 316 outside of the passage 320 in the cannula sleeve 300, the cannula tube 304 can pass through the passage 320, and the cannula tube 304 does not pull on the tether 210.

Figure 11:
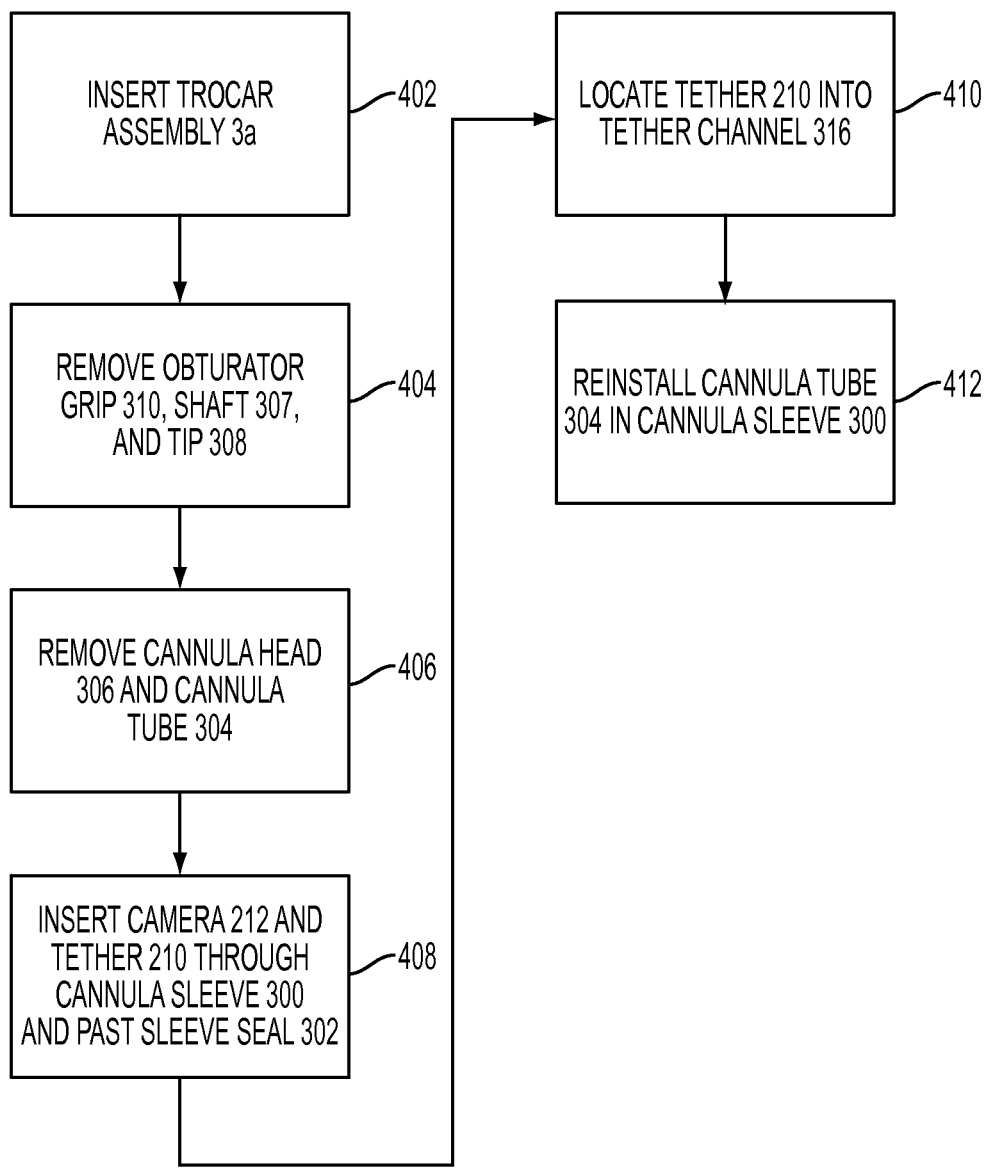
FIG. 11 is a flow chart of method steps for using the trocar assembly of FIG. 10A with a camera and tether.

FIG. 11 shows the steps performed by a surgeon to insert and use the trocar assembly 301 shown in FIGS. 10A-10H. In step 402, the surgeon inserts the trocar assembly 301 through the patient's tissue 102. After the trocar assembly 301 is inserted and properly positioned, in step 404, the obturator grip 310, shaft 307, and tip 308 are removed. Then, in step 406, the cannula head 306 and tube 304 are removed, leaving the cannula sleeve 300. Alternatively, steps 404 and 406 may be combined such that the obturator 310 and cannula 304 are removed from the cannula sleeve 300 simultaneously. In step 408, the surgeon inserts the camera 212 into the passage 320 of the cannula sleeve 300. The surgeon pushes the camera 212 past the sleeve seal 302 so that the camera 212 and a portion of the camera's tether 210 are in the interior body cavity 103. Then, in step 410, the surgeon locates the portion of the tether 210 passing through the cannula sleeve 300 into the tether channel 316. Then, in step 412, the surgeon reinserts the cannula tube 304 or another endoscopic surgical instrument into the cannula sleeve 300.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, nose, anus, and/or vagina) or via a trocar through a relatively small—keyhole—incision incisions (usually 0.5-2.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

All materials used that are in contact with a patient are preferably made of biocompatible materials.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A cannula assembly for a surgical trocar assembly, comprising:
   a housing comprising a distal end defining an opening and a proximal end defining an opening, wherein the housing includes a passage therethrough between the opening at the distal end and the opening at the proximal end, wherein the passage defines an axis, wherein the distal end is configured to receive a cannula tube aligned with the opening at the distal end, and wherein the opening at the proximal end is larger than the opening at the distal end;
   a plurality of compliant membranes arranged as a stack disposed in the passage between the distal end and the proximal end, each of the compliant membranes including an aperture, wherein the passage is configured to receive a surgical instrument therethrough, and wherein the surgical instrument is configured to move through the passage to enter a body cavity of a patient to perform a surgical procedure; and
   a cannula upper housing defining a sidewall, the cannula upper housing removably attachable to the proximal end of the housing, the cannula upper housing defining a port formed within the sidewall, the port defining an aperture to receive a camera tether through the sidewall, wherein the aperture is configured to substantially seal the camera tether passing therethrough, wherein the port is orthogonal to the axis, wherein the port is proximal to the plurality of compliant membranes, and wherein the passage is configured to receive the camera tether therethrough.

2. The cannula assembly of claim 1, wherein the plurality of compliant membranes comprises a first compliant membrane defining a first aperture and a second compliant membrane defining a second aperture.

3. The cannula assembly of claim 2, wherein the first aperture and the second aperture do not overlap.

4. The cannula assembly of claim 2, wherein the first compliant membrane defines a circle, wherein the second compliant membrane defines a circle, wherein the first aperture of the first compliant membrane comprises a circle, wherein the second aperture of the second compliant membrane comprises a circle, wherein the first aperture is offset from the center of the first compliant membrane, wherein the second aperture is offset from the center of the second compliant membrane, and wherein the first aperture and the second aperture do not overlap.

5. The cannula assembly of claim 1, wherein at least a portion of each of the plurality of compliant membranes is made of at least one of silicone, latex, and rubber.

6. The cannula assembly of claim 1, wherein the housing further comprises a plurality of first engagement members in the passage;
   each of the plurality of compliant membranes comprises a plurality of second engagement members; and
   the second engagement members of each membrane couple to the first engagement members such that at least a portion of each compliant membrane is stretched between the first engagement members.

7. The cannula assembly of claim 6, wherein the passage defines a periphery and the plurality of first engagement members comprises a plurality of posts arranged around the periphery of the passage; and
   wherein each membrane defines a periphery and the plurality of second engagement members of each membrane comprises a plurality of holes around the periphery of each membrane, and wherein each of the plurality of holes around the periphery of each membrane aligns with one of the plurality of posts around the periphery of the passage.

8. The cannula assembly of claim 1, further comprising a retaining ring that is selectively attachable to the passage, wherein the retaining ring retains the stack of the plurality of compliant membranes in the passage when the retaining ring is attached to the passage.

9. The cannula assembly of claim 1, further comprising a cannula tube attached to the distal end of the housing.

10. The cannula assembly of claim 1, wherein the port includes a compliant gasket disposed therein, the compliant gasket defining an orifice.

11. A trocar assembly comprising the cannula assembly of claim 1, and further comprising:
   a cannula tube attached to the distal end of the housing;

an obturator, comprising an obturator shaft having a length greater than a combined length of the housing and the cannula tube, the obturator shaft configured to be slidingly received by the passage through the housing and the cannula tube; and wherein each aperture in each of the plurality of compliant membranes is dimensioned to accommodate passage of the obturator shaft therethrough.

12. The cannula assembly of claim 1, wherein the port is formed transversely through the sidewall.

13. The cannula assembly of claim 1, further comprising a plurality of thumb screws, wherein the housing further comprising a plurality of buttresses, wherein each of the thumb screws comprises a post configured to be matingly received by a corresponding buttress, and wherein the thumb screws are configured to releasably attach the cannula upper housing to the housing.

14. The cannula assembly of claim 13, wherein the plurality of buttresses comprises a first buttress and a second buttress, wherein the first buttress is located on an outer perimeter of the housing, wherein the second buttress is located on the outer perimeter of the housing, and wherein the first buttress is diametrically opposed to the second buttress.

15. The cannula assembly of claim 1, wherein the camera tether is configured to be biased towards the side of the passage along the axis through the passage.

16. A cannula assembly for a surgical trocar assembly, comprising:

a lower housing comprising a lower distal end comprising a lower distal opening and a lower proximal end comprising a lower proximal opening, wherein the lower housing defines a lower passage therethrough between the lower distal opening and the lower proximal opening, wherein the lower distal end is configured to receive a cannula tube aligned with the lower distal opening, and wherein the lower proximal opening is larger than the lower distal opening;

a plurality of compliant membranes arranged as a stack disposed in the passage between the lower distal end and the lower proximal end, each of the compliant membranes comprising an aperture, and wherein the lower passage is configured to receive a surgical instrument therethrough; and an upper housing comprising an upper distal end comprising an upper distal opening and an upper proximal end comprising an upper proximal opening, wherein the upper housing defines an upper passage therethrough between the upper distal opening and the upper proximal opening, wherein the upper distal end is configured to couplably attach to the lower proximal end, wherein the upper passage defines a sidewall, and wherein the sidewall defines a port configured to sealably receive a camera tether passing therethrough, wherein the port is proximal to the plurality of compliant membranes, and wherein the lower passage is configured to receive the camera tether therethrough.

17. The cannula assembly of claim 16, wherein the port is formed transversely through the sidewall.

18. The cannula assembly of claim 16, wherein the cannula assembly defines a central passage therethrough extending between the lower distal opening and the upper proximal opening, wherein the central passage defines a longitudinal axis, and wherein the port is formed transversely to the longitudinal axis.

19. The cannula assembly of claim 18, wherein the camera tether is configured to be biased towards the side of the lower passage along the longitudinal axis.

20. The cannula assembly of claim 16, further comprising a plurality of thumb screws, wherein the lower housing further comprising a plurality of buttresses, wherein each of the thumb screws comprises a post configured to be matingly received by a corresponding buttress, and wherein the thumb screws are configured to releasably attach the upper housing to the lower housing.

21. The cannula assembly of claim 20, wherein the plurality of buttresses comprises a first buttress and a second buttress, wherein the first buttress is located on an outer perimeter of the lower housing, wherein the second buttress is located on the outer perimeter of the outer housing, and wherein the first buttress is diametrically opposed to the second buttress.

22. The cannula assembly of claim 16, wherein the plurality of compliant membranes comprises a first compliant membrane defining a circle and second compliant membrane defining a circle, wherein a first aperture of the first compliant membrane comprises a circle, wherein a second aperture of the second compliant membrane comprises a circle, wherein the first aperture is offset from the center of the first compliant membrane, wherein the second aperture is offset from the center of the second compliant membrane, and wherein the first aperture and the second aperture do not overlap.

\* \* \* \* \*